United States Patent [19]

Bushell et al.

[11] Patent Number: 4,987,141

[45] Date of Patent: Jan. 22, 1991

[54] INSECTICIDAL COMPOUNDS AND COMPOSITIONS

[75] Inventors: Michael J. Bushell; Robin A. E. Carr, both of Wokingham; Donn W. Moseley; Nan C. Sillars, both of Reading, all of England

[73] Assignee: Imperial Chemical Industries PLC, London, England

[21] Appl. No.: 391,241

[22] Filed: Aug. 9, 1989

[30] Foreign Application Priority Data

Aug. 24, 1988 [GB] United Kingdom ................. 8820115

[51] Int. Cl.[5] .................... A01N 43/40; C07D 213/64

[52] U.S. Cl. .................................... 514/346; 514/335; 514/517; 546/293; 546/261; 558/48

[58] Field of Search ............... 514/346, 335, 336, 517; 546/294, 261, 284, 293; 558/48

[56] References Cited

U.S. PATENT DOCUMENTS 2,211,702 8/1940 Naegeli .............................. 546/261

FOREIGN PATENT DOCUMENTS 0182603 5/1986 European Pat. Off. .

OTHER PUBLICATIONS

Kato et al., *J. Pesticide Sci.*, 13:107-115 (1988).

*Primary Examiner*—Mary C. Lee
*Assistant Examiner*—Jacqueline Haley
*Attorney, Agent, or Firm*—Cushman, Darby & Cushman

[57] ABSTRACT

The invention provides insecticidally active compounds of formula:

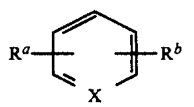

wherein X is N or CH; $R^a$ is the group $(R^1)(R^2)NS(O)_n$—wherein $R^1$ and $R^2$ are independently selected from H, alkyl, haloalkyl, alkoxy, alkoxyalkyl, formyl, alkanoyl, alkenyl, alkynyl, optionally substituted cycloalkyl, optionally substituted cycloalkylmethyl, optionally substituted benzyl and optionally substituted phenyl, and n is 0, 1 or 2; $R^b$ is the group $—OSO_2R^3$ wherein $R^3$ is alkyl optionally substituted by an optionally substituted phenyl group, haloalkyl, alkenyl optionally substituted by an optionally substituted phenyl group, optionally substituted aryl or $N(R^4)(R^5)$, wherein $R^4$ and $R^5$ are independently selected from H and alkyl; and wherein the groups $R^a$ and $R^b$ occupy either a 1,3 configuration relative to each other when X is CH, or a 2,4 or 2,6 configuration relative to X when X is N. The invention provides insecticidal compositions comprising these compounds and methods of their use in controlling insects and also provides processes and intermediates for preparing the compounds.

9 Claims, No Drawings

INSECTICIDAL COMPOUNDS AND COMPOSITIONS

This invention relates to novel insecticidally active compounds, to compositions comprising them and methods of their use in combating insect pests, and to novel intermediates and chemical processes useful in their preparation.

Insecticidal activity has been reported for alkylthiophenyl sulphonates and oxidised derivatives in Japanese Patent Publication J68/003898 and in Japanese Patent Application No J48/098025, and also by Kato et al in Journal of Pesticide Science, Volume 13, pages 107–115 (1988). Insecticidal and nematocidal activity has also been described for alkylthiopyrid-2-yl sulphonates and oxidised derivatives in European Patent Application No 0182603. The present invention is based on the discovery of high levels of insecticidal activity for novel pyridyl and phenyl sulphonates having a sulphonamide substituent, or a reduced form thereof, on the pyridine or benzene ring such that the two substituents are arranged in a 1,3configuration relative to each other. The compounds of the invention exhibit particularly high levels of control of target insect pests and are characterised by an excellent level of systemic activity.

In a first aspect the invention provides a compound of formula (I):

(I)

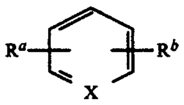

wherein X is nitrogen or carbon bearing a hydrogen atom; $R^a$ is a group of formula $(R^1)(R^2)NS(O)_n$— wherein $R^1$ and $R^2$ are independently selected from hydrogen, $C_{1-8}$ alkyl, $C_{1-6}$ haloalkyl, $C_{1-6}$ alkoxy, $C_{2-6}$ alkoxyalkyl, formyl, $C_{2-6}$ alkanoyl, $C_{2-8}$ alkenyl, $C_{2-8}$ alkynyl, optionally substituted $C_{3-6}$ cycloalkyl, optionally substituted $C_{3-6}$ cycloalkylmethyl, optionally substituted phenyl and optionally substituted benzyl, and n is 0, 1 or 2; $R^b$ is a group of formula —$OSO_2R^3$ wherein $R^3$ is selected from $C_{1-8}$ alkyl, $C_{1-4}$ alkyl substituted by an optionally substituted phenyl group, $C_{1-8}$ haloalkyl, $C_{2-6}$ alkenyl, $C_{2-4}$ alkenyl substituted by an optionally substituted phenyl group, optionally substituted aryl, and a group of formula —$N(R^4)(R^5)$ wherein $R^4$ and $R^5$ are independently selected from hydrogen and $C_{1-4}$ alkyl; and wherein the groups $R^a$ and $R^b$ occupy either a 1,3 configuration relative to each other on the ring when X is carbon bearing a hydrogen, or a 2,4 or 2,6 configuration relative to the group X when X is nitrogen.

The terms alkyl, haloalkyl, alkoxy, alkoxyalkyl, alkanoyl, alkenyl and alkynyl as used herein include within their scope both straight and branched chain varieties.

Suitable examples of the groups $R^1$ and $R^2$ are hydrogen, $C_{1-7}$ alkyl, for example methyl, ethyl, n-propyl, 1-methylethyl, n-butyl, 1-methylpropyl, 2-methylpropyl, 1,1-dimethylethyl, n-pentyl, 2,2-dimethylpropyl, pent-2-yl, n-hexyl, hex-2-yl, n-heptyl or hept-2-yl; $C_{1-4}$ haloalkyl, for example fluoromethyl, difluoromethyl, trifluoromethyl, 2,2,2-trifluoroethyl, pentafluoroethyl, 3,3,3-trifluoropropyl, 1-trifluoromethylethyl or 2,2,3,3,3-pentafluoropropyl; $C_{1-4}$ alkoxy, for example methoxy, ethoxy, propoxy or 1-methylethoxy; $C_{2-4}$ alkoxyalkyl, for example methoxymethyl or methoxyethyl; formyl; $C_{2-4}$ alkanoyl, for example acetyl or propanoyl; $C_{2-4}$ alkenyl, for example prop-2-en-1-yl; $C_{2-4}$ alkynyl, for example prop-2-yn-1-yl; optionally substituted $C_{3-6}$ cycloalkyl, for example cyclopropyl; optionally substituted $C_{3-6}$ cycloalkylmethyl, for example cyclopropylmethyl; optionally substituted phenyl or optionally substituted benzyl.

Suitable examples of the group $R^3$ are $C_{1-4}$ alkyl, for example methyl, ethyl, n-propyl, 1-methylethyl, n-butyl, 2-methylpropyl or 1,1-dimethylethyl; $C_{1-2}$ alkyl substituted with an optionally substituted phenyl group, for example phenylmethyl or 2-phenylethyl; $C_{1-6}$ haloalkyl, for example fluoromethyl, difluoromethyl, trifluoromethyl, chloromethyl, dichloromethyl, trichloromethyl, 2,2,2-trifluoroethyl, 1,1,2,2,2-pentaflouroethyl, 2,2,2-trichloromethyl, 3-chloropropyl, 3-fluoropropyl, or perfluoro-n-hexyl; $C_{2-4}$ alkenyl, for example ethenyl or prop-2-en-1-yl; ethenyl optionally substituted with an optionally substituted phenyl group, for example 2-phenylethenyl; optionally substituted phenyl, for example phenyl or a 4-substituted phenyl group such as 4-methylphenyl, 4-trifluoromethylphenyl or 4-methoxyphenyl; optionally substituted pyridyl, for example pyrid-2-yl or 6-fluoro-2-pyridyl; 2-thienyl; 3-thienyl; or a group of formula —$N(R^4)(R^5)$ wherein $R^4$ and $R^5$ are independently selected from hydrogen and $C_{1-4}$ alkyl, for example methylamino, ethylamino, dimethylamino or diethylamino.

A preferred group of compounds according to the invention comprises any of those compounds of formula (I) described hereinabove wherein the value of n is 2.

A further preferred group of compounds according to the invention comprises any of those compounds of formula (I) described hereinabove wherein the group X is nitrogen.

A further preferred group of compounds according to the invention are those of formula (IA):

(IA)

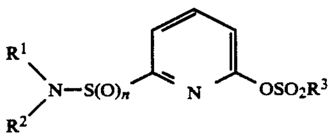

wherein $R^1$ and $R^2$ are independently selected from hydrogen, $C_{1-6}$ alkyl, $C_{1-6}$ haloalkyl, $C_{1-6}$ alkoxy, $C_{1-6}$ alkoxyalkyl, formyl, $C_{2-6}$ alkanoyl, $C_{3-6}$ cycloalkyl, optionally substituted phenyl and optionally substituted benzyl; $R^3$ is selected from $C_{1-6}$ alkyl, $C_{1-6}$ haloalkyl and a group of formula —$N(R^4)(R^5)$ where $R^4$ and $R^5$ are independently selected from hydrogen and $C_{1-6}$ alkyl; and n is selected from 0, 1 and 2.

A particularly preferred group of compounds according to the invention are those according to formula (IA) wherein the value of n is 2; one of $R^1$ and $R^2$ is $C_{1-4}$ alkyl, $C_{1-3}$ haloalkyl, $C_{2-3}$ alkynyl, cyclopropyl or cyclopropylmethyl, and the other is either hydrogen, $C_{1-4}$ alkyl, $C_{1-3}$ haloalkyl, $C_{2-3}$ alkynyl, cyclopropyl or cyclopropylmethyl; and $R^3$ is methyl.

Compounds according to this invention which are to be considered as being specifically disclosed herein are presented in Tables IA, IB and IC.

TABLE IA

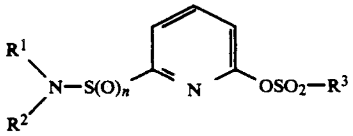

| COMPOUND NO. | $R^1$ | $R^2$ | n | $R^3$ |
|---|---|---|---|---|
| 1 | $CH(CH_3)_2$ | H | 2 | $CH_3$ |
| 2 | $CH(CH_3)_2$ | $CH_3$ | 2 | $CH_3$ |
| 3 | cyclopropyl | H | 2 | $CH_3$ |
| 4 | $CH(CH_3)_2$ | $CH_3$ | 2 | 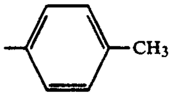 |
| 5 | $CH_2CF_3$ | H | 2 | $CH_3$ |
| 6 | $COCH_3$ | H | 2 | $CH_3$ |
| 7 | $CH(CH_3)(CH_2)_4CH_3$ | H | 2 | $CH_3$ |
| 8 | $OCH_3$ | $CH_3$ | 2 | $CH_3$ |
| 9 | $CH_2CH_2OCH_3$ | H | 2 | $CH_3$ |
| 10 | phenyl | H | 2 | $CH_3$ |
| 11 | $CH(CH_3)CH_2CH_3$ | H | 2 | $CH_3$ |
| 12 | $CH(CH_3)CH_2CH_3$ | H | 2 | $C_2H_5$ |
| 13 | $CH(CH_3)_2$ | H | 2 | $CF_3$ |
| 14 | $CH(CH_3)_2$ | H | 2 | $C_2H_5$ |
| 15 | $CH(CH_3)_2$ | $CH_3$ | 2 | $C_2H_5$ |
| 16 | $CH(CH_3)_2$ | $CH_3$ | 2 | $CF_3$ |
| 17 | $CH(CH_3)_2$ | H | 2 | $CH_2CF_3$ |
| 18 | $CH(CH_3)_2$ | H | 2 | phenyl |
| 19 | $CH(CH_3)_2$ | H | 2 | 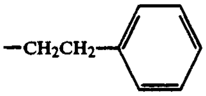 |
| 20 | $CH(CH_3)_2$ | H | 2 | $CH_2CH_2CH_3$ |
| 21 | $CH(CH_3)_2$ | H | 2 | $(CF_2)_5CF_3$ |
| 22 | $CH(CH_3)_2$ | H | 2 | $(CH_2)_3CH_3$ |
| 23 | $CH(CH_3)_2$ | H | 2 | 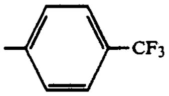 |
| 24 | $CH(CH_3)_2$ | H | 2 | 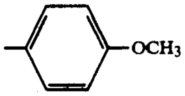 |
| 25 | $CH(CH_3)_2$ | H | 2 | 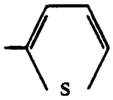 |
| 26 | $CH(CH_3)_2$ | H | 2 | $CH_2Cl$ |
| 27 | $CH(CH_3)_2$ | H | 2 | $CH_2CH_2CH_2Cl$ |
| 28 | $CH(CH_3)_2$ | H | 2 | 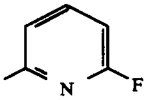 |
| 29 | $CH(CH_3)_2$ | H | 2 | 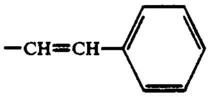 |
| 30 | $CH(CH_3)_2$ | H | 2 | $CHCl_2$ |

TABLE IA-continued

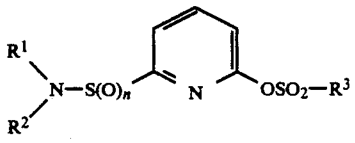

| COMPOUND NO. | $R^1$ | $R^2$ | n | $R^3$ |
|---|---|---|---|---|
| 31 | 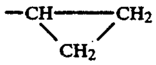 | H | 2 | $C_2H_5$ |
| 32 | H | H | 2 | $CH_3$ |
| 33 | $CH(CH_3)_2$ | H | 2 | $CH{=}CH_2$ |
| 34 | $CH(CH_3)_2$ | $CH(CH_3)_2$ | 2 | $CH_3$ |
| 35 | 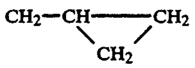 | $CH_3$ | 2 | $CH_3$ |
| 36 | $(CH_2)_2CH_3$ | $(CH_2)_2CH_3$ | 2 | $CH_3$ |
| 37 | $C_2H_5$ | $C_2H_5$ | 2 | $CH_3$ |
| 38 | $(CH_2)_2CH_3$ | $CH_3$ | 2 | $CH_3$ |
| 39 | $CH_3$ | $CH_3$ | 2 | $CH_3$ |
| 40 | $CH_2CH(CH_3)_2$ | H | 2 | $CH_3$ |
| 41 | $C_2H_5$ | $CH_3$ | 2 | $CH_3$ |
| 42 | $CH_2CF_2CF_3$ | H | 2 | $CH_3$ |
| 43 | $CH_2CH_2CH_2Cl$ | $CH_3$ | 2 | $CH_3$ |
| 44 | $CH(CH_3)CF_3$ | H | 2 | $CH_3$ |
| 45 | $(CH_2)_2CF_3$ | H | 2 | $CH_3$ |
| 46 | $CH_3$ | H | 2 | $CH_3$ |
| 47 | $CH_2C{\equiv}CH$ | $CH_3$ | 2 | $CH_3$ |
| 48 | $C(CH_3)_3$ | H | 2 | $CH_3$ |
| 51 | $CH(CH_3)_2$ | H | 0 | $CH_3$ |
| 52 | $CH(CH_3)_2$ | H | 1 | $CH_3$ |
| 53 | $C_2H_5$ | H | 2 | $CH_3$ |
| 54 | $CH_2CH_2CH_3$ | H | 2 | $CH_3$ |
| 55 | $(CH_2)_3CH_3$ | H | 2 | $CH_3$ |
| 56 | 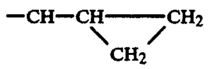 | H | 2 | $CH_3$ |
| 57 | $CH_2C{\equiv}CH$ | H | 2 | $CH_3$ |
| 58 | $CH_2CF_3$ | $CH_3$ | 2 | $CH_3$ |
| 59 | $CH_2CF_2CF_3$ | $CH_3$ | 2 | $CH_3$ |
| 60 | $CH_2CH_2CF_3$ | $CH_3$ | 2 | $CH_3$ |
| 61 | $CH(CF_3)CH_3$ | $CH_3$ | 2 | $CH_3$ |
| 62 | 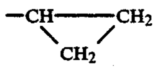 | $CH_3$ | 2 | $CH_3$ |
| 63 | $(CH_2)_3CH_3$ | $CH_3$ | 2 | $CH_3$ |
| 64 | $CH(CH_3)CH_2CH_3$ | $CH_3$ | 2 | $CH_3$ |
| 65 | $CH_2CH(CH_3)_2$ | $CH_3$ | 2 | $CH_3$ |
| 66 | $C(CH_3)_3$ | $CH_3$ | 2 | $CH_3$ |
| 67 | $CH_2CF_3$ | $C_2H_5$ | 2 | $CH_3$ |
| 68 | $CH_2CF_2CF_3$ | $C_2H_5$ | 2 | $CH_3$ |
| 69 | $CH_2CH_2CH_3$ | $C_2H_5$ | 2 | $CH_3$ |
| 70 | $CH_2CH_2CF_3$ | $C_2H_5$ | 2 | $CH_3$ |
| 71 | $CH(CH_3)_2$ | $C_2H_5$ | 2 | $CH_3$ |
| 72 | $CH(CF_3)CH_3$ | $C_2H_5$ | 2 | $CH_3$ |
| 73 | 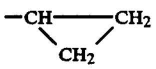 | $C_2H_5$ | 2 | $CH_3$ |
| 74 | $(CH_2)_3CH_3$ | $C_2H_5$ | 2 | $CH_3$ |
| 75 | $CH(CH_3)CH_2CH_3$ | $C_2H_5$ | 2 | $CH_3$ |
| 76 | $CH_2CH(CH_3)_2$ | $C_2H_5$ | 2 | $CH_3$ |
| 77 | $C(CH_3)_3$ | $C_2H_5$ | 2 | $CH_3$ |
| 78 | 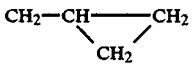 | $C_2H_5$ | 2 | $CH_3$ |
| 79 | $CH_2C{\equiv}CH$ | $C_2H_5$ | 2 | $CH_3$ |
| 80 | $CH_2CF_2CF_3$ | $CH_2CF_3$ | 2 | $CH_3$ |
| 81 | $CH_2CH_2CH_3$ | $CH_2CF_3$ | 2 | $CH_3$ |

TABLE IA-continued

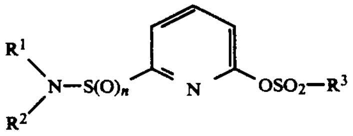

| COMPOUND NO. | $R^1$ | $R^2$ | n | $R^3$ |
|---|---|---|---|---|
| 82 | $CH_2CH_2CF_3$ | $CH_2CF_3$ | 2 | $CH_3$ |
| 83 | $CH(CH_3)_2$ | $CH_2CF_3$ | 2 | $CH_3$ |
| 84 | $CH(CF_3)CH_3$ | $CH_2CF_3$ | 2 | $CH_3$ |
| 85 | 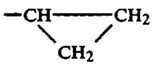 | $CH_2CF_3$ | 2 | $CH_3$ |
| 86 | $(CH_3)_3CH_3$ | $CH_2CF_3$ | 2 | $CH_3$ |
| 87 | $CH(CH_3)CH_2CH_3$ | $CH_2CF_3$ | 2 | $CH_3$ |
| 88 | $CH_2CH(CH_3)_2$ | $CH_2CF_3$ | 2 | $CH_3$ |
| 89 | $C(CH_3)_3$ | $CH_2CF_3$ | 2 | $CH_3$ |
| 90 | 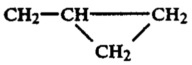 | $CH_2CF_3$ | 2 | $CH_3$ |
| 91 | $CH_2C{\equiv}CH$ | $CH_2CF_3$ | 2 | $CH_3$ |
| 92 | $CH_2CH_2CF_3$ | $CH_2CH_2CH_3$ | 2 | $CH_3$ |
| 93 | $CH(CH_3)_2$ | $CH_2CH_2CH_3$ | 2 | $CH_3$ |
| 94 | $CH(CF_3)CH_3$ | $CH_2CH_2CH_3$ | 2 | $CH_3$ |
| 95 | 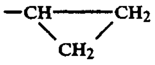 | $CH_2CH_2CH_3$ | 2 | $CH_3$ |
| 96 | $(CH_2)_3CH_3$ | $CH_2CH_2CH_3$ | 2 | $CH_3$ |
| 97 | $CH(CH_3)CH_2CH_3$ | $CH_2CH_2CH_3$ | 2 | $CH_3$ |
| 98 | $CH_2CH(CH_3)_2$ | $CH_2CH_2CH_3$ | 2 | $CH_3$ |
| 99 | $C(CH_3)_3$ | $CH_2CH_2CH_3$ | 2 | $CH_3$ |
| 100 | 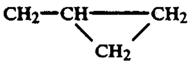 | $CH_2CH_2CH_3$ | 2 | $CH_3$ |
| 101 | $CH_2C{\equiv}CH$ | $CH_2CH_2CH_3$ | 2 | $CH_3$ |
| 102 | $CH_2CF_2CF_3$ | $CH_2CH_2CH_3$ | 2 | $CH_3$ |
| 103 | $CH_2CF_2CF_3$ | $CH_2CH_2CF_3$ | 2 | $CH_3$ |
| 104 | $CH_2CH_2CF_3$ | $CH_2CH_2CF_3$ | 2 | $CH_3$ |
| 105 | $CH(CH_3)_2$ | $CH_2CH_2CF_3$ | 2 | $CH_3$ |
| 106 | $CH(CF_3)CH_3$ | $CH_2CH_2CF_3$ | 2 | $CH_3$ |
| 107 | 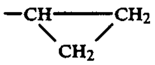 | $CH_2CH_2CF_3$ | 2 | $CH_3$ |
| 108 | $(CH_2)_3CH_3$ | $CH_2CH_2CF_3$ | 2 | $CH_3$ |
| 109 | $CH(CH_3)CH_2CH_3$ | $CH_2CH_2CF_3$ | 2 | $CH_3$ |
| 110 | $CH_2CH(CH_3)_2$ | $CH_2CH_2CF_3$ | 2 | $CH_3$ |
| 111 | $C(CH_3)_3$ | $CH_2CH_2CF_3$ | 2 | $CH_3$ |
| 112 | 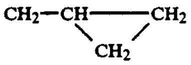 | $CH_2CH_2CF_3$ | 2 | $CH_3$ |
| 113 | $CH_2C\ CH$ | $CH_2CH_2CF_3$ | 2 | $CH_3$ |
| 114 | $CH_2CF_2CF_3$ | $CH(CH_3)_2$ | 2 | $CH_3$ |
| 115 | $CH(CF_3)CH_3$ | $CH(CH_3)_2$ | 2 | $CH_3$ |
| 116 | 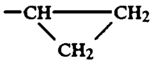 | $CH(CH_3)_2$ | 2 | $CH_3$ |
| 117 | $(CH_2)_3CH_3$ | $CH(CH_3)_2$ | 2 | $CH_3$ |
| 118 | $CH(CH_3)CH_2CH_3$ | $CH(CH_3)_2$ | 2 | $CH_3$ |
| 119 | $CH_2CH(CH_3)_2$ | $CH(CH_3)_2$ | 2 | $CH_3$ |
| 120 | $C(CH_3)_3$ | $CH(CH_3)_2$ | 2 | $CH_3$ |
| 121 | 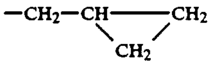 | $CH(CH_3)_2$ | 2 | $CH_3$ |

TABLE IA-continued

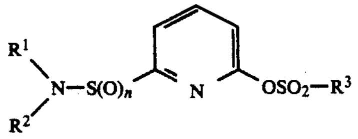

| COMPOUND NO. | $R^1$ | $R^2$ | n | $R^3$ |
|---|---|---|---|---|
| 122 | $CH_2-C\equiv CH$ | $CH(CH_3)_2$ | 2 | $CH_3$ |
| 123 | $CH_2CF_2CF_3$ | $CH(CF_3)CH_3$ | 2 | $CH_3$ |
| 124 | $CH(CF_3)CH_3$ | $CH(CF_3)CH_3$ | 2 | $CH_3$ |
| 125 | 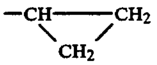 | $CH(CF_3)CH_3$ | 2 | $CH_3$ |
| 126 | $(CH_2)_3CH_3$ | $CH(CF_3)CH_3$ | 2 | $CH_3$ |
| 127 | $CH(CH_3)CH_2CH_3$ | $CH(CF_3)CH_3$ | 2 | $CH_3$ |
| 128 | $CH_2CH(CH_3)_2$ | $CH(CF_3)CH_3$ | 2 | $CH_3$ |
| 129 | $C(CH_3)_3$ | $CH(CF_3)CH_3$ | 2 | $CH_3$ |
| 130 | 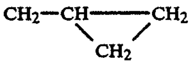 | $CH(CF_3)CH_3$ | 2 | $CH_3$ |
| 131 | $CH_2C\equiv CH$ | $CH(CF_3)CH_3$ | 2 | $CH_3$ |
| 132 | $CH_2CF_2CF_3$ | 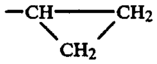 | 2 | $CH_3$ |
| 133 | 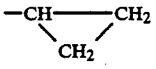 | 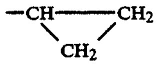 | 2 | $CH_3$ |
| 134 | $(CH_2)_3CH_3$ | 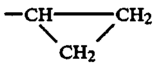 | 2 | $CH_3$ |
| 135 | $CH(CH_3)CH_2CH_3$ | 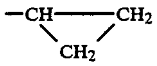 | 2 | $CH_3$ |
| 136 | $CH_2CH(CH_3)_2$ | 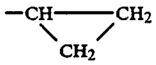 | 2 | $CH_3$ |
| 137 | $C(CH_3)_3$ | 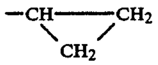 | 2 | $CH_3$ |
| 138 | 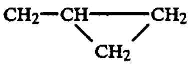 | 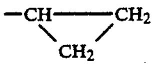 | 2 | $CH_3$ |
| 139 | $CH_2C\equiv CH$ | 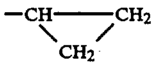 | 2 | $CH_3$ |
| 140 | $CH_2CF_2CF_3$ | $(CH_2)_3CH_3$ | 2 | $CH_3$ |
| 141 | $(CH_2)_3CH_3$ | $(CH_2)_3CH_3$ | 2 | $CH_3$ |
| 142 | $CH(CH_3)CH_2CH_3$ | $(CH_2)_3CH_3$ | 2 | $CH_3$ |
| 143 | $CH_2CH(CH_3)_2$ | $(CH_2)_3CH_3$ | 2 | $CH_3$ |
| 144 | $C(CH_3)_3$ | $(CH_2)_3CH_3$ | 2 | $CH_3$ |
| 145 | 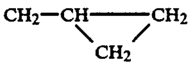 | $(CH_2)_3CH_3$ | 2 | $CH_3$ |
| 146 | $CH_2C\equiv CH$ | $(CH_2)_3CH_3$ | 2 | $CH_3$ |
| 147 | $CH_2CF_2CF_3$ | $CH(CH_3)CH_2CH_3$ | 2 | $CH_3$ |
| 148 | $CH(CH_3)CH_2CH_3$ | $CH(CH_3)CH_2CH_3$ | 2 | $CH_3$ |
| 149 | $CH_2CH(CH_3)_2$ | $CH(CH_3)CH_2CH_3$ | 2 | $CH_3$ |
| 150 | $C(CH_3)_3$ | $CH(CH_3)CH_2CH_3$ | 2 | $CH_3$ |

TABLE IA-continued

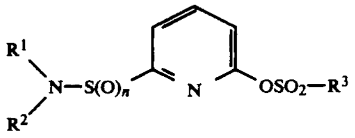

| COMPOUND NO. | $R^1$ | $R^2$ | n | $R^3$ |
|---|---|---|---|---|
| 151 | 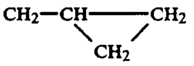 | $CH(CH_3)CH_2CH_3$ | 2 | $CH_3$ |
| 152 | $CH_2C{\equiv}CH$ | $CH(CH_3)CH_2CH_3$ | 2 | $CH_3$ |
| 153 | $CH_2CF_2CF_3$ | $CH_2CH(CH_3)_2$ | 2 | $CH_3$ |
| 154 | $CH_2CH(CH_3)_2$ | $CH_2CH(CH_3)_2$ | 2 | $CH_3$ |
| 155 | $C(CH_3)_3$ | $CH_2CH(CH_3)_2$ | 2 | $CH_3$ |
| 156 | 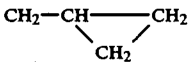 | $CH_2CH(CH_3)_2$ | 2 | $CH_3$ |
| 157 | $CH_2C\ CH$ | $CH_2CH(CH_3)_2$ | 2 | $CH_3$ |
| 158 | $CH_2CF_2CF_3$ | $C(CH_3)_3$ | 2 | $CH_3$ |
| 159 | $C(CH_3)_3$ | $C(CH_3)_3$ | 2 | $CH_3$ |
| 160 | 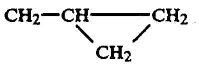 | $C(CH_3)_3$ | 2 | $CH_3$ |
| 161 | $CH_2C{\equiv}CH$ | $C(CH_3)_3$ | 2 | $CH_3$ |
| 162 | $-CH_2CF_2CF_3$ | 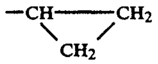 | 2 | $CH_3$ |
| 163 | 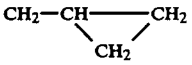 | 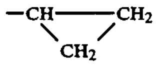 | 2 | $CH_3$ |
| 164 | $CH_2C{\equiv}CH$ | 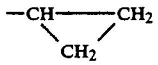 | 2 | $CH_3$ |
| 165 | $CH_2CF_2CF_3$ | $CH_2C{\equiv}CH$ | 2 | $CH_3$ |
| 166 | $CH_2C{\equiv}CH$ | $CH_2C{\equiv}CH$ | 2 | $CH_3$ |
| 167 | $CH_3CF_2CF_3$ | $CH_2CF_2CF_3$ | 2 | $CH_3$ |
| 168 | H | H | 1 | $CH_3$ |
| 169 | $CH_3$ | H | 1 | $CH_3$ |
| 170 | $C_2H_5$ | H | 1 | $CH_3$ |
| 171 | $CH_2CF_3$ | H | 1 | $CH_3$ |
| 172 | $CH_2CF_2CF_3$ | H | 1 | $CH_3$ |
| 173 | $CH_2CH_2CH_3$ | H | 1 | $CH_3$ |
| 174 | $CH_2CH_2CF_3$ | H | 1 | $CH_3$ |
| 175 | $CH(CF_3)CH_3$ | H | 1 | $CH_3$ |
| 176 | 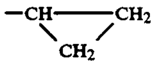 | H | 1 | $CH_3$ |
| 177 | $(CH_2)_3CH_3$ | H | 1 | $CH_3$ |
| 178 | $CH(CH_3)CH_2CH_3$ | H | 1 | $CH_3$ |
| 179 | $CH_2CH(CH_3)_2$ | H | 1 | $CH_3$ |
| 180 | $C(CH_3)_3$ | H | 1 | $CH_3$ |
| 181 | 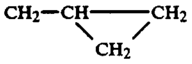 | H | 1 | $CH_3$ |
| 182 | H | $CH_3$ | 1 | $CH_3$ |
| 183 | $CH_3$ | $CH_3$ | 1 | $CH_3$ |
| 184 | $C_2H_5$ | $CH_3$ | 1 | $CH_3$ |
| 185 | $CH_2CF_3$ | $CH_3$ | 1 | $CH_3$ |
| 186 | $CH_2CF_2CF_3$ | $CH_3$ | 1 | $CH_3$ |
| 187 | $CH_2CH_2CH_3$ | $CH_3$ | 1 | $CH_3$ |
| 188 | $CH_2CH_2CF_3$ | $CH_3$ | 1 | $CH_3$ |
| 189 | $CH(CH_3)_2$ | $CH_3$ | 1 | $CH_3$ |
| 190 | $CH(CF_3)CH_3$ | $CH_3$ | 1 | $CH_3$ |

TABLE IA-continued

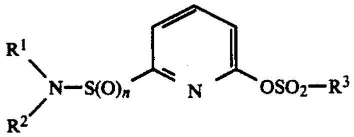

| COMPOUND NO. | $R^1$ | $R^2$ | n | $R^3$ |
|---|---|---|---|---|
| 191 | 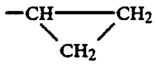 | $CH_3$ | 1 | $CH_3$ |
| 192 | $(CH_2)_3CH_3$ | $CH_3$ | 1 | $CH_3$ |
| 193 | $CH(CH_3)CH_2CH_3$ | $CH_3$ | 1 | $CH_3$ |
| 194 | $CH_2CH(CH_3)_2$ | $CH_3$ | 1 | $CH_3$ |
| 195 | $C(CH_3)_3$ | $CH_3$ | 1 | $CH_3$ |
| 196 | 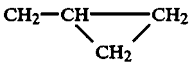 | $CH_3$ | 1 | $CH_3$ |
| 197 | H | H | 0 | $CH_3$ |
| 198 | $CH_3$ | H | 0 | $CH_3$ |
| 199 | $C_2H_5$ | H | 0 | $CH_3$ |
| 200 | $CH_2CF_3$ | H | 0 | $CH_3$ |
| 201 | $CH_2CF_2CF_3$ | H | 0 | $CH_3$ |
| 202 | $CH_2CH_2CH_3$ | H | 0 | $CH_3$ |
| 203 | $CH_2CH_2CF_3$ | H | 0 | $CH_3$ |
| 204 | $CH(CF_3)CH_3$ | H | 0 | $CH_3$ |
| 205 | 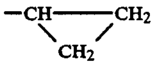 | H | 0 | $CH_3$ |
| 206 | $(CH_2)_3CH_3$ | H | 0 | $CH_3$ |
| 207 | $CH(CH_3)CH_2CH_3$ | H | 0 | $CH_3$ |
| 208 | $CH_2CH(CH_3)_2$ | H | 0 | $CH_3$ |
| 209 | $C(CH_3)_3$ | H | 0 | $CH_3$ |
| 210 | 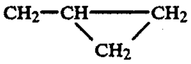 | H | 0 | $CH_3$ |
| 211 | H | $CH_3$ | 0 | $CH_3$ |
| 212 | $CH_3$ | $CH_3$ | 0 | $CH_3$ |
| 213 | $C_2H_5$ | $CH_3$ | 0 | $CH_3$ |
| 214 | $CH_2CF_3$ | $CH_3$ | 0 | $CH_3$ |
| 215 | $CH_2CF_2CF_3$ | $CH_3$ | 0 | $CH_3$ |
| 216 | $CH_2CH_2CH_3$ | $CH_3$ | 0 | $CH_3$ |
| 217 | $CH_2CH_2CF_3$ | $CH_3$ | 0 | $CH_3$ |
| 218 | $CH(CH_3)_2$ | $CH_3$ | 0 | $CH_3$ |
| 219 | $CH(CF_3)CH_3$ | $CH_3$ | 0 | $CH_3$ |
| 220 | 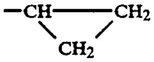 | $CH_3$ | 0 | $CH_3$ |
| 221 | $(CH_2)_3CH_3$ | $CH_3$ | 0 | $CH_3$ |
| 222 | $CH(CH_3)CH_2CH_3$ | $CH_3$ | 0 | $CH_3$ |
| 223 | $CH_2CH(CH_3)_2$ | $CH_3$ | 0 | $CH_3$ |
| 224 | $C(CH_3)_3$ | $CH_3$ | 0 | $CH_3$ |
| 225 | 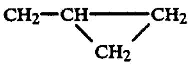 | $CH_3$ | 0 | $CH_3$ |

TABLE IB

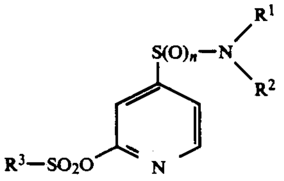

| COMPOUND NO | $R^1$ | $R^2$ | n | $R^3$ |
|---|---|---|---|---|
| 49 | $CH(CH_3)_2$ | H | 2 | $CH_3$ |
| 226 | $CH(CH_3)_2$ | $CH_3$ | 2 | $CH_3$ |
| 227 | cyclopropyl | H | 2 | $CH_3$ |
| 228 | $CH(CH_3)_2$ | $CH_3$ | 2 | 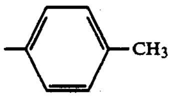 |
| 229 | $CH_2CF_3$ | H | 2 | $CH_3$ |
| 230 | $COCH_3$ | H | 2 | $CH_3$ |
| 231 | $CH(CH_3)(CH_2)_4CH_3$ | H | 2 | $CH_3$ |
| 232 | $OCH_3$ | $CH_3$ | 2 | $CH_3$ |
| 233 | $CH_2CH_2OCH_3$ | H | 2 | $CH_3$ |
| 234 | phenyl | H | 2 | $CH_3$ |
| 235 | $CH(CH_3)CH_2CH_3$ | H | 2 | $CH_3$ |
| 236 | $CH(CH_3)CH_2CH_3$ | H | 2 | $C_2H_5$ |
| 237 | $CH(CH_3)_2$ | H | 2 | $CF_3$ |
| 238 | $CH(CH_3)_2$ | H | 2 | $C_2H_5$ |
| 239 | $CH(CH_3)_2$ | $CH_3$ | 2 | $C_2H_5$ |
| 240 | $CH(CH_3)_2$ | $CH_3$ | 2 | $CF_3$ |
| 241 | $CH(CH_3)_2$ | H | 2 | $CH_2CF_3$ |
| 242 | $CH(CH_3)_2$ | H | 2 | phenyl |
| 243 | $CH(CH_3)_2$ | H | 2 | 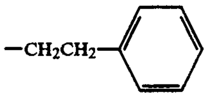 |
| 244 | $CH(CH_3)_2$ | H | 2 | $CH_2CH_2CH_3$ |
| 245 | $CH(CH_3)_2$ | H | 2 | $(CF_2)_5CF_3$ |
| 246 | $CH(CH_3)_2$ | H | 2 | $(CH_2)_3CH_3$ |
| 247 | $CH(CH_3)_2$ | H | 2 | 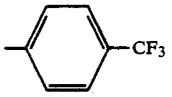 |
| 248 | $CH(CH_3)_2$ | H | 2 | 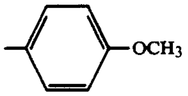 |
| 249 | $CH(CH_3)_2$ | H | 2 | 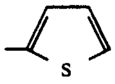 |
| 250 | $CH(CH_3)_2$ | H | 2 | $CH_2Cl$ |
| 251 | $CH(CH_3)_2$ | H | 2 | $CH_2CH_2CH_2Cl$ |
| 252 | $CH(CH_3)_2$ | H | 2 | 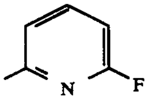 |
| 253 | $CH(CH_3)_2$ | H | 2 | 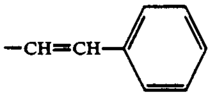 |
| 254 | $CH(CH_3)_2$ | H | 2 | $CHCl_2$ |

TABLE IB-continued

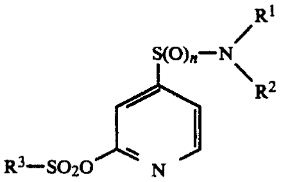

| COMPOUND NO | $R^1$ | $R^2$ | n | $R^3$ |
|---|---|---|---|---|
| 255 | 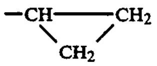 | H | 2 | $C_2H_5$ |
| 256 | H | H | 2 | $CH_3$ |
| 257 | $CH(CH_3)_2$ | H | 2 | $CH{=}CH_2$ |
| 258 | $CH(CH_3)_2$ | $CH(CH_3)_2$ | 2 | $CH_3$ |
| 259 | 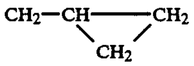 | $CH_3$ | 2 | $CH_3$ |
| 260 | $(CH_2)_2CH_3$ | $(CH_2)_2CH_3$ | 2 | $CH_3$ |
| 261 | $C_2H_5$ | $C_2H_5$ | 2 | $CH_3$ |
| 262 | $(CH_2)_2CH_3$ | $CH_3$ | 2 | $CH_3$ |
| 263 | $CH_3$ | $CH_3$ | 2 | $CH_3$ |
| 264 | $CH_2CH(CH_3)_2$ | H | 2 | $CH_3$ |
| 265 | $C_2H_5$ | $CH_3$ | 2 | $CH_3$ |
| 266 | $CH_2CF_2CF_3$ | H | 2 | $CH_3$ |
| 267 | $CH_2CH_2CH_2Cl$ | $CH_3$ | 2 | $CH_3$ |
| 268 | $CH(CH_3)CF_3$ | H | 2 | $CH_3$ |
| 269 | $(CH_2)_2CF_3$ | H | 2 | $CH_3$ |
| 270 | $CH_3$ | H | 2 | $CH_3$ |
| 271 | $CH_2C{\equiv}CH$ | $CH_3$ | 2 | $CH_3$ |
| 272 | $C(CH_3)_3$ | H | 2 | $CH_3$ |
| 273 | $CH(CH_3)_2$ | H | 0 | $CH_3$ |
| 274 | $CH(CH_3)_2$ | H | 1 | $CH_3$ |
| 275 | $C_2H_5$ | H | 2 | $CH_3$ |
| 276 | $CH_2CH_2CH_3$ | H | 2 | $CH_3$ |
| 277 | $(CH_2)_3CH_3$ | H | 2 | $CH_3$ |
| 278 | 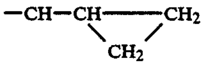 | H | 2 | $CH_3$ |
| 279 | $CH_2C{\equiv}CH$ | H | 2 | $CH_3$ |
| 280 | $CH_2CF_3$ | $CH_3$ | 2 | $CH_3$ |
| 281 | $CH_2CF_2CF_3$ | $CH_3$ | 2 | $CH_3$ |
| 282 | $CH_2CH_2CF_3$ | $CH_3$ | 2 | $CH_3$ |
| 283 | $CH(CF_3)CH_3$ | $CH_3$ | 2 | $CH_3$ |
| 284 | 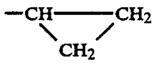 | $CH_3$ | 2 | $CH_3$ |
| 285 | $(CH_2)_3CH_3$ | $CH_3$ | 2 | $CH_3$ |
| 286 | $CH(CH_3)CH_2CH_3$ | $CH_3$ | 2 | $CH_3$ |
| 287 | $CH_2CH(CH_3)_2$ | $CH_3$ | 2 | $CH_3$ |
| 288 | $C(CH_3)_3$ | $CH_3$ | 2 | $CH_3$ |
| 289 | $CH_2CF_3$ | $C_2H_5$ | 2 | $CH_3$ |
| 290 | $CH_2CF_2CF_3$ | $C_2H_5$ | 2 | $CH_3$ |
| 291 | $CH_2CH_2CH_3$ | $C_2H_5$ | 2 | $CH_3$ |
| 292 | $CH_2CH_2CF_3$ | $C_2H_5$ | 2 | $CH_3$ |
| 293 | $CH(CH_3)_2$ | $C_2H_5$ | 2 | $CH_3$ |
| 294 | $CH(CF_3)CH_3$ | $C_2H_5$ | 2 | $CH_3$ |
| 295 | 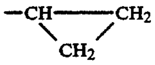 | $C_2H_5$ | 2 | $CH_3$ |
| 296 | $(CH_2)_3CH_3$ | $C_2H_5$ | 2 | $CH_3$ |
| 297 | $CH(CH_3)CH_2CH_3$ | $C_2H_5$ | 2 | $CH_3$ |
| 298 | $CH_2CH(CH_3)_2$ | $C_2H_5$ | 2 | $CH_3$ |
| 299 | $C(CH_3)_3$ | $C_2H_5$ | 2 | $CH_3$ |
| 300 | 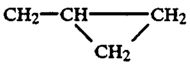 | $C_2H_5$ | 2 | $CH_3$ |
| 301 | $CH_2C{\equiv}CH$ | $C_2H_5$ | 2 | $CH_3$ |

TABLE IB-continued

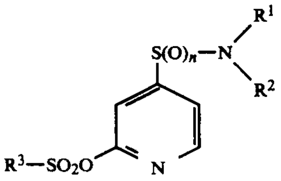

| COMPOUND NO | $R^1$ | $R^2$ | n | $R^3$ |
|---|---|---|---|---|
| 302 | $CH_2CF_2CF_3$ | $CH_2CF_3$ | 2 | $CH_3$ |
| 303 | $CH_2CH_2CH_3$ | $CH_2CF_3$ | 2 | $CH_3$ |
| 304 | $CH_2CH_2CF_3$ | $CH_2CF_3$ | 2 | $CH_3$ |
| 305 | $CH(CH_3)_2$ | $CH_2CF_3$ | 2 | $CH_3$ |
| 306 | $CH(CF_3)CH_3$ | $CH_2CF_3$ | 2 | $CH_3$ |
| 307 | 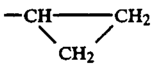 | $CH_2CF_3$ | 2 | $CH_3$ |
| 308 | $(CH_2)_3CH_3$ | $CH_2CF_3$ | 2 | $CH_3$ |
| 309 | $CH(CH_3)CH_2CH_3$ | $CH_2CF_3$ | 2 | $CH_3$ |
| 310 | $CH_2CH(CH_3)_2$ | $CH_2CF_3$ | 2 | $CH_3$ |
| 311 | $C(CH_3)_3$ | $CH_2CF_3$ | 2 | $CH_3$ |
| 312 | 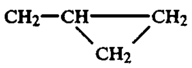 | $CH_2CF_3$ | 2 | $CH_3$ |
| 313 | $CH_2C{\equiv}CH$ | $CH_2CF_3$ | 2 | $CH_3$ |
| 314 | $CH_2CH_2CF_3$ | $CH_2CH_2CH_3$ | 2 | $CH_3$ |
| 315 | $CH(CH_3)_2$ | $CH_2CH_2CH_3$ | 2 | $CH_3$ |
| 316 | $CH(CF_3)CH_3$ | $CH_2CH_2CH_3$ | 2 | $CH_3$ |
| 317 | 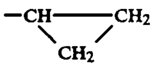 | $CH_2CH_2CH_3$ | 2 | $CH_3$ |
| 318 | $(CH_2)_3CH_3$ | $CH_2CH_2CH_3$ | 2 | $CH_3$ |
| 319 | $CH(CH_3)CH_2CH_3$ | $CH_2CH_2CH_3$ | 2 | $CH_3$ |
| 320 | $CH_2CH(CH_3)_2$ | $CH_2CH_2CH_3$ | 2 | $CH_3$ |
| 321 | $C(CH_3)_3$ | $CH_2CH_2CH_3$ | 2 | $CH_3$ |
| 322 | 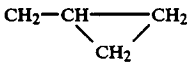 | $CH_2CH_2CH_3$ | 2 | $CH_3$ |
| 323 | $CH_2C\ CH$ | $CH_2CH_2CH_3$ | 2 | $CH_3$ |
| 324 | $CH_2CF_2CF_3$ | $CH_2CH_2CH_3$ | 2 | $CH_3$ |
| 325 | $CH_2CF_2CF_3$ | $CH_2CH_2CF_3$ | 2 | $CH_3$ |
| 326 | $CH_2CH_2CF_3$ | $CH_2CH_2CF_3$ | 2 | $CH_3$ |
| 327 | $CH(CH_3)_2$ | $CH_2CH_2CF_3$ | 2 | $CH_3$ |
| 328 | $CH(CF_3)CH_3$ | $CH_2CH_2CF_3$ | 2 | $CH_3$ |
| 329 | 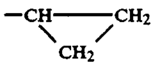 | $CH_2CH_2CF_3$ | 2 | $CH_3$ |
| 330 | $(CH_2)_3CH_3$ | $CH_2CH_2CF_3$ | 2 | $CH_3$ |
| 331 | $CH(CH_3)CH_2CH_3$ | $CH_2CH_2CF_3$ | 2 | $CH_3$ |
| 332 | $CH_2CH(CH_3)_2$ | $CH_2CH_2CF_3$ | 2 | $CH_3$ |
| 333 | $C(CH_3)_3$ | $CH_2CH_2CF_3$ | 2 | $CH_3$ |
| 334 | 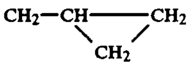 | $CH_2CH_2CF_3$ | 2 | $CH_3$ |
| 335 | $CH_2C\ CH$ | $CH_2CH_2CF_3$ | 2 | $CH_3$ |
| 336 | $CH_2CF_2CF_3$ | $CH(CH_3)_2$ | 2 | $CH_3$ |
| 337 | $CH(CF_3)CH_3$ | $CH(CH_3)_2$ | 2 | $CH_3$ |
| 338 | 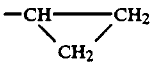 | $CH(CH_3)_2$ | 2 | $CH_3$ |
| 339 | $(CH_2)_3CH_3$ | $CH(CH_3)_2$ | 2 | $CH_3$ |
| 340 | $CH(CH_3)CH_2CH_3$ | $CH(CH_3)_2$ | 2 | $CH_3$ |
| 341 | $CH_2CH(CH_3)_2$ | $CH(CH_3)_2$ | 2 | $CH_3$ |
| 342 | $C(CH_3)_3$ | $CH(CH_3)_2$ | 2 | $CH_3$ |

TABLE IB-continued

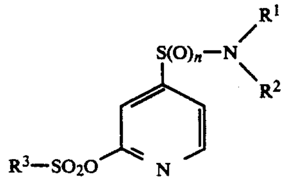

| COMPOUND NO | $R^1$ | $R^2$ | n | $R^3$ |
|---|---|---|---|---|
| 343 | 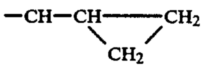 | $CH(CH_3)_2$ | 2 | $CH_3$ |
| 344 | $CH_2—C≡CH$ | $CH(CH_3)_2$ | 2 | $CH_3$ |
| 345 | $CH_2CF_2CF_3$ | $CH(CF_3)CH_3$ | 2 | $CH_3$ |
| 346 | $CH(CF_3)CH_3$ | $CH(CF_3)CH_3$ | 2 | $CH_3$ |
| 347 | 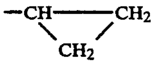 | $CH(CF_3)CH_3$ | 2 | $CH_3$ |
| 348 | $(CH_2)_3CH_3$ | $CH(CF_3)CH_3$ | 2 | $CH_3$ |
| 349 | $CH(CH_3)CH_2CH_3$ | $CH(CF_3)CH_3$ | 2 | $CH_3$ |
| 350 | $CH_2CH(CH_3)_2$ | $CH(CF_3)CH_3$ | 2 | $CH_3$ |
| 351 | $C(CH_3)_3$ | $CH(CF_3)CH_3$ | 2 | $CH_3$ |
| 352 | 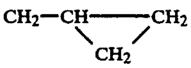 | $CH(CF_3)CH_3$ | 2 | $CH_3$ |
| 353 | $CH_2C≡CH$ | $CH(CF_3)CH_3$ | 2 | $CH_3$ |
| 354 | $CH_2CF_2CF_3$ | 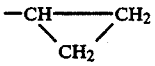 | 2 | $CH_3$ |
| 355 | 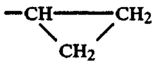 | 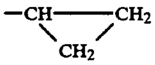 | 2 | $CH_3$ |
| 356 | $(CH_2)_3CH_3$ | 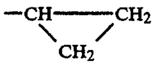 | 2 | $CH_3$ |
| 357 | $CH(CH_3)CH_2CH_3$ | 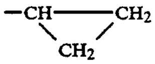 | 2 | $CH_3$ |
| 358 | $CH_2CH(CH_3)_2$ | 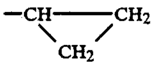 | 2 | $CH_3$ |
| 359 | $C(CH_3)_3$ | 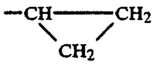 | 2 | $CH_3$ |
| 360 | 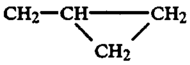 | 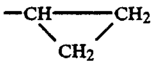 | 2 | $CH_3$ |
| 361 | $CH_2C≡CH$ | 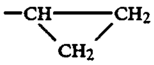 | 2 | $CH_3$ |
| 362 | $CH_2CF_2CF_3$ | $(CH_2)_3CH_3$ | 2 | $CH_3$ |
| 363 | $(CH_2)_3CH_3$ | $(CH_2)_3CH_3$ | 2 | $CH_3$ |
| 364 | $CH(CH_3)CH_2CH_3$ | $(CH_2)_3CH_3$ | 2 | $CH_3$ |
| 365 | $CH_2CH(CH_3)_2$ | $(CH_2)_3CH_3$ | 2 | $CH_3$ |
| 366 | $C(CH_3)_3$ | $(CH_2)_3CH_3$ | 2 | $CH_3$ |
| 367 | 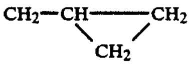 | $(CH_2)_3CH_3$ | 2 | $CH_3$ |
| 368 | $CH_2C≡CH$ | $(CH_2)_3CH_3$ | 2 | $CH_3$ |
| 369 | $CH_2CF_2CF_3$ | $CH(CH_3)CH_2CH_3$ | 2 | $CH_3$ |
| 370 | $CH(CH_3)CH_2CH_3$ | $CH(CH_3)CH_2CH_3$ | 2 | $CH_3$ |

TABLE IB-continued

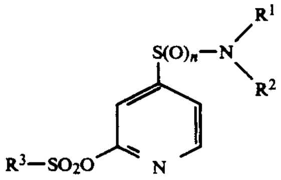

| COMPOUND NO | $R^1$ | $R^2$ | n | $R^3$ |
|---|---|---|---|---|
| 371 | $CH_2CH(CH_3)_2$ | $CH(CH_3)CH_2CH_3$ | 2 | $CH_3$ |
| 372 | $C(CH_3)_3$ | $CH(CH_3)CH_2CH_3$ | 2 | $CH_3$ |
| 373 | 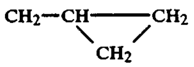 | $CH(CH_3)CH_2CH_3$ | 2 | $CH_3$ |
| 374 | $CH_2C{\equiv}CH$ | $CH(CH_3)CH_2CH_3$ | 2 | $CH_3$ |
| 375 | $CH_2CF_2CF_3$ | $CH_2CH(CH_3)_2$ | 2 | $CH_3$ |
| 376 | $CH_2CH(CH_3)_2$ | $CH_2CH(CH_3)_2$ | 2 | $CH_3$ |
| 377 | $C(CH_3)_3$ | $CH_2CH(CH_3)_2$ | 2 | $CH_3$ |
| 378 | 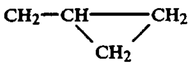 | $CH_2CH(CH_3)_2$ | 2 | $CH_3$ |
| 379 | $CH_2C{\equiv}CH$ | $CH_2CH(CH_3)_2$ | 2 | $CH_3$ |
| 380 | $CH_2CF_2CF_3$ | $C(CH_3)_3$ | 2 | $CH_3$ |
| 381 | $C(CH_3)_3$ | $C(CH_3)_3$ | 2 | $CH_3$ |
| 382 | 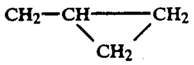 | $C(CH_3)_3$ | 2 | $CH_3$ |
| 383 | $CH_2C{\equiv}CH$ | $C(CH_3)_3$ | 2 | $CH_3$ |
| 384 | $-CH_2CF_2CF_3$ | 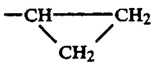 | 2 | $CH_3$ |
| 385 | 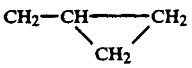 | 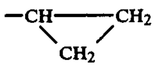 | 2 | $CH_3$ |
| 386 | $CH_2C{\equiv}CH$ | 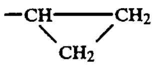 | 2 | $CH_3$ |
| 387 | $CH_2CF_2CF_3$ | $CH_2C{\equiv}CH$ | 2 | $CH_3$ |
| 388 | $CH_2C{\equiv}CH$ | $CH_2C{\equiv}CH$ | 2 | $CH_3$ |
| 389 | $CH_3CF_2CF_3$ | $CH_2CF_2CF_3$ | 2 | $CH_3$ |
| 390 | H | H | 1 | $CH_3$ |
| 391 | $CH_3$ | H | 1 | $CH_3$ |
| 392 | $C_2H_5$ | H | 1 | $CH_3$ |
| 393 | $CH_2CF_3$ | H | 1 | $CH_3$ |
| 394 | $CH_2CF_2CF_3$ | H | 1 | $CH_3$ |
| 395 | $CH_2CH_2CH_3$ | H | 1 | $CH_3$ |
| 396 | $CH_2CH_2CF_3$ | H | 1 | $CH_3$ |
| 397 | $CH(CF_3)CH_3$ | H | 1 | $CH_3$ |
| 398 | 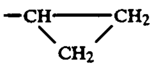 | H | 1 | $CH_3$ |
| 399 | $(CH_2)_3CH_3$ | H | 1 | $CH_3$ |
| 400 | $CH(CH_3)CH_2CH_3$ | H | 1 | $CH_3$ |
| 401 | $CH_2CH(CH_3)_2$ | H | 1 | $CH_3$ |
| 402 | $C(CH_3)_3$ | H | 1 | $CH_3$ |
| 403 | 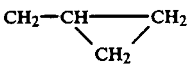 | H | 1 | $CH_3$ |
| 404 | H | $CH_3$ | 1 | $CH_3$ |
| 405 | $CH_3$ | $CH_3$ | 1 | $CH_3$ |
| 406 | $C_2H_5$ | $CH_3$ | 1 | $CH_3$ |
| 407 | $CH_2CF_3$ | $CH_3$ | 1 | $CH_3$ |
| 408 | $CH_2CF_2CF_3$ | $CH_3$ | 1 | $CH_3$ |
| 409 | $CH_2CH_2CH_3$ | $CH_3$ | 1 | $CH_3$ |
| 410 | $CH_2CH_2CF_3$ | $CH_3$ | 1 | $CH_3$ |
| 411 | $CH(CH_3)_2$ | $CH_3$ | 1 | $CH_3$ |

TABLE IB-continued

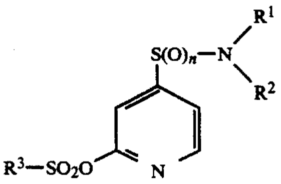

| COMPOUND NO | $R^1$ | $R^2$ | n | $R^3$ |
|---|---|---|---|---|
| 412 | $CH(CF_3)CH_3$ | $CH_3$ | 1 | $CH_3$ |
| 413 | 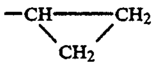 | $CH_3$ | 1 | $CH_3$ |
| 414 | $(CH_2)_3CH_3$ | $CH_3$ | 1 | $CH_3$ |
| 415 | $CH(CH_3)CH_2CH_3$ | $CH_3$ | 1 | $CH_3$ |
| 416 | $CH_2CH(CH_3)_2$ | $CH_3$ | 1 | $CH_3$ |
| 417 | $C(CH_3)_3$ | $CH_3$ | 1 | $CH_3$ |
| 418 | 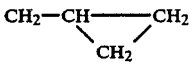 | $CH_3$ | 1 | $CH_3$ |
| 419 | H | H | 0 | $CH_3$ |
| 420 | $CH_3$ | H | 0 | $CH_3$ |
| 421 | $C_2H_5$ | H | 0 | $CH_3$ |
| 422 | $CH_2CF_3$ | H | 0 | $CH_3$ |
| 423 | $CH_2CF_2CF_3$ | H | 0 | $CH_3$ |
| 424 | $CH_2CH_2CH_3$ | H | 0 | $CH_3$ |
| 425 | $CH_2CH_2CF_3$ | H | 0 | $CH_3$ |
| 426 | $CH(CF_3)CH_3$ | H | 0 | $CH_3$ |
| 427 | 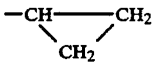 | H | 0 | $CH_3$ |
| 428 | $(CH_2)_3CH_3$ | H | 0 | $CH_3$ |
| 429 | $CH(CH_3)CH_2CH_3$ | H | 0 | $CH_3$ |
| 430 | $CH_2CH(CH_3)_2$ | H | 0 | $CH_3$ |
| 431 | $C(CH_3)_3$ | H | 0 | $CH_3$ |
| 432 | 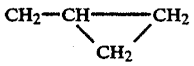 | H | 0 | $CH_3$ |
| 433 | H | $CH_3$ | 0 | $CH_3$ |
| 434 | $CH_3$ | $CH_3$ | 0 | $CH_3$ |
| 435 | $C_2H_5$ | $CH_3$ | 0 | $CH_3$ |
| 436 | $CH_2CF_3$ | $CH_3$ | 0 | $CH_3$ |
| 437 | $CH_2CF_2CF_3$ | $CH_3$ | 0 | $CH_3$ |
| 438 | $CH_2CH_2CH_3$ | $CH_3$ | 0 | $CH_3$ |
| 439 | $CH_2CH_2CF_3$ | $CH_3$ | 0 | $CH_3$ |
| 440 | $CH(CH_3)_2$ | $CH_3$ | 0 | $CH_3$ |
| 441 | $CH(CF_3)CH_3$ | $CH_3$ | 0 | $CH_3$ |
| 442 | 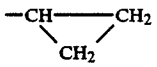 | $CH_3$ | 0 | $CH_3$ |
| 443 | $(CH_2)_3CH_3$ | $CH_3$ | 0 | $CH_3$ |
| 444 | $CH(CH_3)CH_2CH_3$ | $CH_3$ | 0 | $CH_3$ |
| 445 | $CH_2CH(CH_3)_2$ | $CH_3$ | 0 | $CH_3$ |
| 446 | $C(CH_3)_3$ | $CH_3$ | 0 | $CH_3$ |
| 447 | 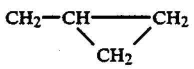 | $CH_3$ | 0 | $CH_3$ |

TABLE IC

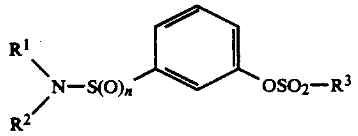

| COMPOUND NO | $R^1$ | $R^2$ | n | $R^3$ |
|---|---|---|---|---|
| 50 | $CH(CH_3)_2$ | H | 2 | $CH_3$ |
| 448 | $CH(CH_3)_2$ | $CH_3$ | 2 | $CH_3$ |
| 449 | cyclopropyl | H | 2 | $CH_3$ |
| 450 | $CH(CH_3)_2$ | $CH_3$ | 2 | 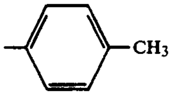 |
| 451 | $CH_2CF_3$ | H | 2 | $CH_3$ |
| 452 | $COCH_3$ | H | 2 | $CH_3$ |
| 453 | $CH(CH_3)(CH_2)_4CH_3$ | H | 2 | $CH_3$ |
| 454 | $OCH_3$ | $CH_3$ | 2 | $CH_3$ |
| 455 | $CH_2CH_2OCH_3$ | H | 2 | $CH_3$ |
| 456 | phenyl | H | 2 | $CH_3$ |
| 457 | $CH(CH_3)CH_2CH_3$ | H | 2 | $CH_3$ |
| 458 | $CH(CH_3)CH_2CH_3$ | H | 2 | $C_2H_5$ |
| 459 | $CH(CH_3)_2$ | H | 2 | $CF_3$ |
| 460 | $CH(CH_3)_2$ | H | 2 | $C_2H_5$ |
| 461 | $CH(CH_3)_2$ | $CH_3$ | 2 | $C_2H_5$ |
| 462 | $CH(CH_3)_2$ | $CH_3$ | 2 | $CF_3$ |
| 463 | $CH(CH_3)_2$ | H | 2 | $CH_2CF_3$ |
| 464 | $CH(CH_3)_2$ | H | 2 | phenyl |
| 465 | $CH(CH_3)_2$ | H | 2 | 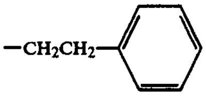 |
| 466 | $CH(CH_3)_2$ | H | 2 | $CH_2CH_2CH_3$ |
| 467 | $CH(CH_3)_2$ | H | 2 | $(CF_2)_5CF_3$ |
| 468 | $CH(CH_3)_2$ | H | 2 | $(CH_2)_3CH_3$ |
| 469 | $CH(CH_3)_2$ | H | 2 | 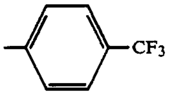 |
| 470 | $CH(CH_3)_2$ | H | 2 | 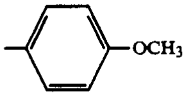 |
| 471 | $CH(CH_3)_2$ | H | 2 | 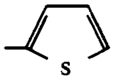 |
| 472 | $CH(CH_3)_2$ | H | 2 | $CH_2Cl$ |
| 473 | $CH(CH_3)_2$ | H | 2 | $CH_2CH_2CH_2Cl$ |
| 474 | $CH(CH_3)_2$ | H | 2 | 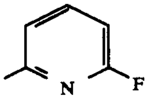 |
| 475 | $CH(CH_3)_2$ | H | 2 | 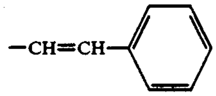 |
| 476 | $CH(CH_3)_2$ | H | 2 | $CHCl_2$ |
| 477 | 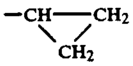 | H | 2 | $C_2H_5$ |

TABLE IC-continued

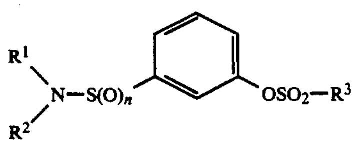

| COMPOUND NO | $R^1$ | $R^2$ | n | $R^3$ |
|---|---|---|---|---|
| 478 | H | H | 2 | $CH_3$ |
| 479 | $CH(CH_3)_2$ | H | 2 | $CH{=}CH_2$ |
| 480 | $CH(CH_3)_2$ | $CH(CH_3)_2$ | 2 | $CH_3$ |
| 481 | 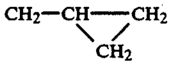 | $CH_3$ | 2 | $CH_3$ |
| 482 | $(CH_2)_2CH_3$ | $(CH_2)_2CH_3$ | 2 | $CH_3$ |
| 483 | $C_2H_5$ | $C_2H_5$ | 2 | $CH_3$ |
| 484 | $(CH_2)_2CH_3$ | $CH_3$ | 2 | $CH_3$ |
| 485 | $CH_3$ | $CH_3$ | 2 | $CH_3$ |
| 486 | $CH_2CH(CH_3)_2$ | H | 2 | $CH_3$ |
| 487 | $C_2H_5$ | $CH_3$ | 2 | $CH_3$ |
| 488 | $CH_2CF_2CF_3$ | H | 2 | $CH_3$ |
| 489 | $CH_2CH_2CH_2Cl$ | $CH_3$ | 2 | $CH_3$ |
| 490 | $CH(CH_3)CF_3$ | H | 2 | $CH_3$ |
| 491 | $(CH_2)_2CF_3$ | H | 2 | $CH_3$ |
| 492 | $CH_3$ | H | 2 | $CH_3$ |
| 493 | $CH_2C{\equiv}CH$ | $CH_3$ | 2 | $CH_3$ |
| 494 | $C(CH_3)_3$ | H | 2 | $CH_3$ |
| 495 | $CH(CH_3)_2$ | H | 0 | $CH_3$ |
| 496 | $CH(CH_3)_2$ | H | 1 | $CH_3$ |
| 497 | $C_2H_5$ | H | 2 | $CH_3$ |
| 498 | $CH_2CH_2CH_3$ | H | 2 | $CH_3$ |
| 499 | $(CH_2)_3CH_3$ | H | 2 | $CH_3$ |
| 500 | 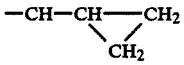 | H | 2 | $CH_3$ |
| 501 | $CH_2C{\equiv}CH$ | H | 2 | $CH_3$ |
| 502 | $CH_2CF_3$ | $CH_3$ | 2 | $CH_3$ |
| 503 | $CH_2CF_2CF_3$ | $CH_3$ | 2 | $CH_3$ |
| 504 | $CH_2CH_2CF_3$ | $CH_3$ | 2 | $CH_3$ |
| 505 | $CH(CF_3)CH_3$ | $CH_3$ | 2 | $CH_3$ |
| 506 | 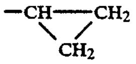 | $CH_3$ | 2 | $CH_3$ |
| 507 | $(CH_2)_3CH_3$ | $CH_3$ | 2 | $CH_3$ |
| 508 | $CH(CH_3)CH_2CH_3$ | $CH_3$ | 2 | $CH_3$ |
| 509 | $CH_2CH(CH_3)_2$ | $CH_3$ | 2 | $CH_3$ |
| 510 | $C(CH_3)_3$ | $CH_3$ | 2 | $CH_3$ |
| 511 | $CH_2CF_3$ | $C_2H_5$ | 2 | $CH_3$ |
| 512 | $CH_2CF_2CF_3$ | $C_2H_5$ | 2 | $CH_3$ |
| 513 | $CH_2CH_2CH_3$ | $C_2H_5$ | 2 | $CH_3$ |
| 514 | $CH_2CH_2CF_3$ | $C_2H_5$ | 2 | $CH_3$ |
| 515 | $CH(CH_3)_2$ | $C_2H_5$ | 2 | $CH_3$ |
| 516 | $CH(CF_3)CH_3$ | $C_2H_5$ | 2 | $CH_3$ |
| 517 | 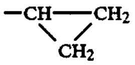 | $C_2H_5$ | 2 | $CH_3$ |
| 518 | $(CH_2)_3CH_3$ | $C_2H_5$ | 2 | $CH_3$ |
| 519 | $CH(CH_3)CH_2CH_3$ | $C_2H_5$ | 2 | $CH_3$ |
| 520 | $CH_2CH(CH_3)_2$ | $C_2H_5$ | 2 | $CH_3$ |
| 521 | $C(CH_3)_3$ | $C_2H_5$ | 2 | $CH_3$ |
| 522 | 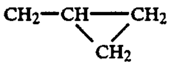 | $C_2H_5$ | 2 | $CH_3$ |
| 523 | $CH_2C{\equiv}CH$ | $C_2H_5$ | 2 | $CH_3$ |
| 524 | $CH_2CF_2CF_3$ | $CH_2CF_3$ | 2 | $CH_3$ |
| 525 | $CH_2CH_2CH_3$ | $CH_2CF_3$ | 2 | $CH_3$ |
| 526 | $CH_2CH_2CF_3$ | $CH_2CF_3$ | 2 | $CH_3$ |
| 527 | $CH(CH_3)_2$ | $CH_2CF_3$ | 2 | $CH_3$ |
| 528 | $CH(CF_3)CH_3$ | $CH_2CF_3$ | 2 | $CH_3$ |

TABLE IC-continued

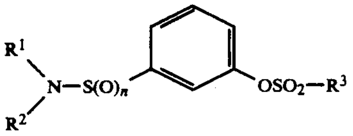

| COMPOUND NO | $R^1$ | $R^2$ | n | $R^3$ |
|---|---|---|---|---|
| 529 | 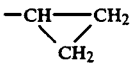 | $CH_2CF_3$ | 2 | $CH_3$ |
| 530 | $(CH_2)_3CH_3$ | $CH_2CF_3$ | 2 | $CH_3$ |
| 531 | $CH(CH_3)CH_2CH_3$ | $CH_2CF_3$ | 2 | $CH_3$ |
| 532 | $CH_2CH(CH_3)_2$ | $CH_2CF_3$ | 2 | $CH_3$ |
| 533 | $C(CH_3)_3$ | $CH_2CF_3$ | 2 | $CH_3$ |
| 534 | 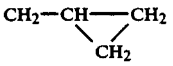 | $CH_2CF_3$ | 2 | $CH_3$ |
| 535 | $CH_2C{\equiv}CH$ | $CH_2CF_3$ | 2 | $CH_3$ |
| 536 | $CH_2CH_2CF_3$ | $CH_2CH_2CH_3$ | 2 | $CH_3$ |
| 537 | $CH(CH_3)_2$ | $CH_2CH_2CH_3$ | 2 | $CH_3$ |
| 538 | $CH(CF_3)CH_3$ | $CH_2CH_2CH_3$ | 2 | $CH_3$ |
| 539 | 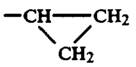 | $CH_2CH_2CH_3$ | 2 | $CH_3$ |
| 540 | $(CH_2)_3CH_3$ | $CH_2CH_2CH_3$ | 2 | $CH_3$ |
| 541 | $CH(CH_3)CH_2CH_3$ | $CH_2CH_2CH_3$ | 2 | $CH_3$ |
| 542 | $CH_2CH(CH_3)_2$ | $CH_2CH_2CH_3$ | 2 | $CH_3$ |
| 543 | $C(CH_3)_3$ | $CH_2CH_2CH_3$ | 2 | $CH_3$ |
| 544 | 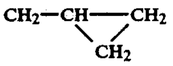 | $CH_2CH_2CH_3$ | 2 | $CH_3$ |
| 545 | $CH_2C{\equiv}CH$ | $CH_2CH_2CH_3$ | 2 | $CH_3$ |
| 546 | $CH_2CF_2CF_3$ | $CH_2CH_2CH_3$ | 2 | $CH_3$ |
| 547 | $CH_2CF_2CF_3$ | $CH_2CH_2CF_3$ | 2 | $CH_3$ |
| 548 | $CH_2CH_2CF_3$ | $CH_2CH_2CF_3$ | 2 | $CH_3$ |
| 549 | $CH(CH_3)_2$ | $CH_2CH_2CF_3$ | 2 | $CH_3$ |
| 550 | $CH(CF_3)CH_3$ | $CH_2CH_2CF_3$ | 2 | $CH_3$ |
| 551 | 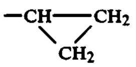 | $CH_2CH_2CF_3$ | 2 | $CH_3$ |
| 552 | $(CH_2)_3CH_3$ | $CH_2CH_2CF_3$ | 2 | $CH_3$ |
| 553 | $CH(CH_3)CH_2CH_3$ | $CH_2CH_2CF_3$ | 2 | $CH_3$ |
| 554 | $CH_2CH(CH_3)_2$ | $CH_2CH_2CF_3$ | 2 | $CH_3$ |
| 555 | $C(CH_3)_3$ | $CH_2CH_2CF_3$ | 2 | $CH_3$ |
| 556 | 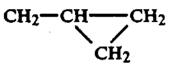 | $CH_2CH_2CF_3$ | 2 | $CH_3$ |
| 557 | $CH_2C{\equiv}CH$ | $CH_2CH_2CF_3$ | 2 | $CH_3$ |
| 558 | $CH_2CF_2CF_3$ | $CH(CH_3)_2$ | 2 | $CH_3$ |
| 559 | $CH(CF_3)CH_3$ | $CH(CH_3)_2$ | 2 | $CH_3$ |
| 560 | 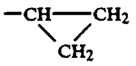 | $CH(CH_3)_2$ | 2 | $CH_3$ |
| 561 | $(CH_2)_3CH_3$ | $CH(CH_3)_2$ | 2 | $CH_3$ |
| 562 | $CH(CH_3)CH_2CH_3$ | $CH(CH_3)_2$ | 2 | $CH_3$ |
| 563 | $CH_2CH(CH_3)_2$ | $CH(CH_3)_2$ | 2 | $CH_3$ |
| 564 | $C(CH_3)_3$ | $CH(CH_3)_2$ | 2 | $CH_3$ |
| 565 | 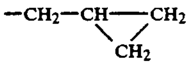 | $CH(CH_3)_2$ | 2 | $CH_3$ |
| 566 | $CH_2{-}C{\equiv}CH$ | $CH(CH_3)_2$ | 2 | $CH_3$ |
| 567 | $CH_2CF_2CF_3$ | $CH(CF_3)CH_3$ | 2 | $CH_3$ |

TABLE IC-continued

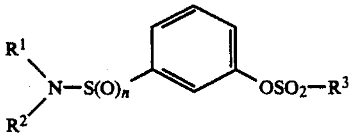

| COMPOUND NO | $R^1$ | $R^2$ | n | $R^3$ |
|---|---|---|---|---|
| 568 | $CH(CF_3)CH_3$ | $CH(CF_3)CH_3$ | 2 | $CH_3$ |
| 569 | 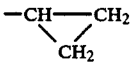 | $CH(CF_3)CH_3$ | 2 | $CH_3$ |
| 570 | $(CH_2)_3CH_3$ | $CH(CF_3)CH_3$ | 2 | $CH_3$ |
| 571 | $CH(CH_3)CH_2CH_3$ | $CH(CF_3)CH_3$ | 2 | $CH_3$ |
| 572 | $CH_2CH(CH_3)_2$ | $CH(CF_3)CH_3$ | 2 | $CH_3$ |
| 573 | $C(CH_3)_3$ | $CH(CF_3)CH_3$ | 2 | $CH_3$ |
| 574 | 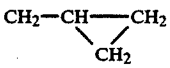 | $CH(CF_3)CH_3$ | 2 | $CH_3$ |
| 575 | $CH_2C{\equiv}CH$ | $CH(CF_3)CH_3$ | 2 | $CH_3$ |
| 576 | $CH_2CF_2CF_3$ | 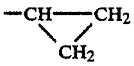 | 2 | $CH_3$ |
| 577 | 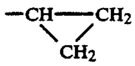 | 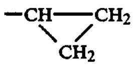 | 2 | $CH_3$ |
| 578 | $(CH_2)_3CH_3$ | 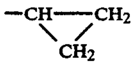 | 2 | $CH_3$ |
| 579 | $CH(CH_3)CH_2CH_3$ | 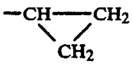 | 2 | $CH_3$ |
| 580 | $CH_2CH(CH_3)_2$ | 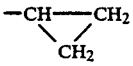 | 2 | $CH_3$ |
| 581 | $C(CH_3)_3$ | 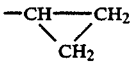 | 2 | $CH_3$ |
| 582 | 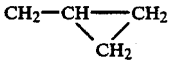 | 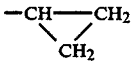 | 2 | $CH_3$ |
| 583 | $CH_2C{\equiv}CH$ | 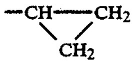 | 2 | $CH_3$ |
| 584 | $CH_2CF_2CF_3$ | $(CH_2)_3CH_3$ | 2 | $CH_3$ |
| 585 | $(CH_2)_3CH_3$ | $(CH_2)_3CH_3$ | 2 | $CH_3$ |
| 586 | $CH(CH_3)CH_2CH_3$ | $(CH_2)_3CH_3$ | 2 | $CH_3$ |
| 587 | $CH_2CH(CH_3)_2$ | $(CH_2)_3CH_3$ | 2 | $CH_3$ |
| 588 | $C(CH_3)_3$ | $(CH_2)_3CH_3$ | 2 | $CH_3$ |
| 589 | 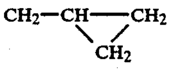 | $(CH_2)_3CH_3$ | 2 | $CH_3$ |
| 590 | $CH_2C{\equiv}CH$ | $(CH_2)_3CH_3$ | 2 | $CH_3$ |
| 591 | $CH_2CF_2CF_3$ | $CH(CH_3)CH_2CH_3$ | 2 | $CH_3$ |
| 592 | $CH(CH_3)CH_2CH_3$ | $CH(CH_3)CH_2CH_3$ | 2 | $CH_3$ |
| 593 | $CH_2CH(CH_3)_2$ | $CH(CH_3)CH_2CH_3$ | 2 | $CH_3$ |
| 594 | $C(CH_3)_3$ | $CH(CH_3)CH_2CH_3$ | 2 | $CH_3$ |
| 595 | 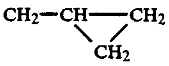 | $CH(CH_3)CH_2CH_3$ | 2 | $CH_3$ |
| 596 | $CH_2C{\equiv}CH$ | $CH(CH_3)CH_2CH_3$ | 2 | $CH_3$ |

TABLE IC-continued

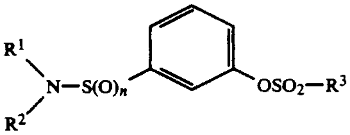

| COMPOUND NO | $R^1$ | $R^2$ | n | $R^3$ |
|---|---|---|---|---|
| 597 | $CH_2CF_2CF_3$ | $CH_2CH(CH_3)_2$ | 2 | $CH_3$ |
| 598 | $CH_2CH(CH_3)_2$ | $CH_2CH(CH_3)_2$ | 2 | $CH_3$ |
| 599 | $C(CH_3)_3$ | $CH_2CH(CH_3)_2$ | 2 | $CH_3$ |
| 600 | 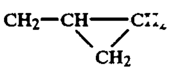 | $CH_2CH(CH_3)_2$ | 2 | $CH_3$ |
| 601 | $CH_2C{\equiv}CH$ | $CH_2CH(CH_3)_2$ | 2 | $CH_3$ |
| 602 | $CH_2CF_2CF_3$ | $C(CH_3)_3$ | 2 | $CH_3$ |
| 603 | $C(CH_3)_3$ | $C(CH_3)_3$ | 2 | $CH_3$ |
| 604 | 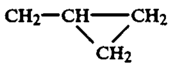 | $C(CH_3)_3$ | 2 | $CH_3$ |
| 605 | $CH_2C{\equiv}CH$ | $C(CH_3)_3$ | 2 | $CH_3$ |
| 606 | $-CH_2CF_2CF_3$ | 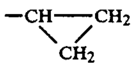 | 2 | $CH_3$ |
| 607 | 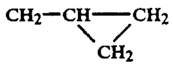 | 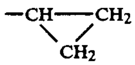 | 2 | $CH_3$ |
| 608 | $CH_2C{\equiv}CH$ | 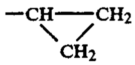 | 2 | $CH_3$ |
| 609 | $CH_2CF_2CF_3$ | $CH_2C{\equiv}CH$ | 2 | $CH_3$ |
| 610 | $CH_2C{\equiv}CH$ | $CH_2C{\equiv}CH$ | 2 | $CH_3$ |
| 611 | $CH_3CF_2CF_3$ | $CH_2CF_2CF_3$ | 2 | $CH_3$ |
| 612 | H | H | 1 | $CH_3$ |
| 613 | $CH_3$ | H | 1 | $CH_3$ |
| 614 | $C_2H_5$ | H | 1 | $CH_3$ |
| 615 | $CH_2CF_3$ | H | 1 | $CH_3$ |
| 616 | $CH_2CF_2CF_3$ | H | 1 | $CH_3$ |
| 617 | $CH_2CH_2CH_3$ | H | 1 | $CH_3$ |
| 618 | $CH_2CH_2CF_3$ | H | 1 | $CH_3$ |
| 619 | $CH(CF_3)CH_3$ | H | 1 | $CH_3$ |
| 620 | 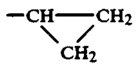 | H | 1 | $CH_3$ |
| 621 | $(CH_2)_3CH_3$ | H | 1 | $CH_3$ |
| 622 | $CH(CH_3)CH_2CH_3$ | H | 1 | $CH_3$ |
| 623 | $CH_2CH(CH_3)_2$ | H | 1 | $CH_3$ |
| 624 | $C(CH_3)_3$ | H | 1 | $CH_3$ |
| 625 | 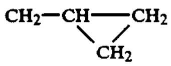 | H | 1 | $CH_3$ |
| 626 | H | $CH_3$ | 1 | $CH_3$ |
| 627 | $CH_3$ | $CH_3$ | 1 | $CH_3$ |
| 628 | $C_2H_5$ | $CH_3$ | 1 | $CH_3$ |
| 629 | $CH_2CF_3$ | $CH_3$ | 1 | $CH_3$ |
| 630 | $CH_2CF_2CF_3$ | $CH_3$ | 1 | $CH_3$ |
| 631 | $CH_2CH_2CH_3$ | $CH_3$ | 1 | $CH_3$ |
| 632 | $CH_2CH_2CF_3$ | $CH_3$ | 1 | $CH_3$ |
| 633 | $CH(CH_3)_2$ | $CH_3$ | 1 | $CH_3$ |
| 634 | $CH(CF_3)CH_3$ | $CH_3$ | 1 | $CH_3$ |
| 635 | 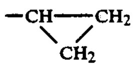 | $CH_3$ | 1 | $CH_3$ |
| 636 | $(CH_2)_3CH_3$ | $CH_3$ | 1 | $CH_3$ |
| 637 | $CH(CH_3)CH_2CH_3$ | $CH_3$ | 1 | $CH_3$ |

TABLE IC-continued

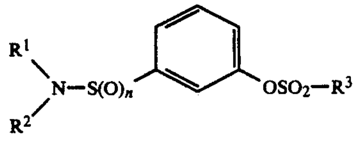

| COMPOUND NO | $R^1$ | $R^2$ | n | $R^3$ |
|---|---|---|---|---|
| 638 | $CH_2CH(CH_3)_2$ | $CH_3$ | 1 | $CH_3$ |
| 639 | $C(CH_3)_3$ | $CH_3$ | 1 | $CH_3$ |
| 640 | 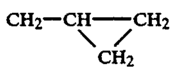 | $CH_3$ | 1 | $CH_3$ |
| 641 | H | H | 0 | $CH_3$ |
| 642 | $CH_3$ | H | 0 | $CH_3$ |
| 643 | $C_2H_5$ | H | 0 | $CH_3$ |
| 644 | $CH_2CF_3$ | H | 0 | $CH_3$ |
| 645 | $CH_2CF_2CF_3$ | H | 0 | $CH_3$ |
| 646 | $CH_2CH_2CH_3$ | H | 0 | $CH_3$ |
| 647 | $CH_2CH_2CF_3$ | H | 0 | $CH_3$ |
| 648 | $CH(CF_3)CH_3$ | H | 0 | $CH_3$ |
| 649 | 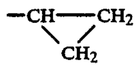 | H | 0 | $CH_3$ |
| 650 | $(CH_2)_3CH_3$ | H | 0 | $CH_3$ |
| 651 | $CH(CH_3)CH_2CH_3$ | H | 0 | $CH_3$ |
| 652 | $CH_2CH(CH_3)_2$ | H | 0 | $CH_3$ |
| 653 | $C(CH_3)_3$ | H | 0 | $CH_3$ |
| 654 | 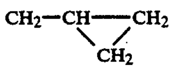 | H | 0 | $CH_3$ |
| 655 | H | $CH_3$ | 0 | $CH_3$ |
| 656 | $CH_3$ | $CH_3$ | 0 | $CH_3$ |
| 657 | $C_2H_5$ | $CH_3$ | 0 | $CH_3$ |
| 658 | $CH_2CF_3$ | $CH_3$ | 0 | $CH_3$ |
| 659 | $CH_2CF_2CF_3$ | $CH_3$ | 0 | $CH_3$ |
| 660 | $CH_2CH_2CH_3$ | $CH_3$ | 0 | $CH_3$ |
| 661 | $CH_2CH_2CF_3$ | $CH_3$ | 0 | $CH_3$ |
| 662 | $CH(CH_3)_2$ | $CH_3$ | 0 | $CH_3$ |
| 663 | $CH(CF_3)CH_3$ | $CH_3$ | 0 | $CH_3$ |
| 664 | 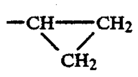 | $CH_3$ | 0 | $CH_3$ |
| 665 | $(CH_2)_3CH_3$ | $CH_3$ | 0 | $CH_3$ |
| 666 | $CH(CH_3)CH_2CH_3$ | $CH_3$ | 0 | $CH_3$ |
| 667 | $CH_2CH(CH_3)_2$ | $CH_3$ | 0 | $CH_3$ |
| 668 | $C(CH_3)_3$ | $CH_3$ | 0 | $CH_3$ |
| 669 | 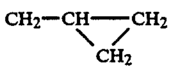 | $CH_3$ | 0 | $CH_3$ |

Compounds according to this invention fall into different structural types according to the particular nature of the group X in Formula (I) and the position of substitution of the groups $R^a$ and $R^b$ relative thereto. The selection of an appropriate synthetic process for the preparation of the compounds of the invention is dependent upon the particular structural type which it is desired to prepare. Compounds of formula (I) in which X is nitrogen and the groups $R^a$ and $R^b$ occupy the 6 and 2 positions respectively relative thereto may be described by Formula (IA):

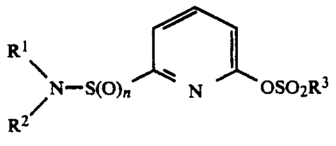

(IA)

wherein $R^1$, $R^2$, $R^3$ and n have any of the values given hereinbefore. Compounds of formula (I) in which X is nitrogen and the groups $R^a$ and $R^b$ occupy the 4 and 2 positions respectively relative thereto may be described by Formula (IB):

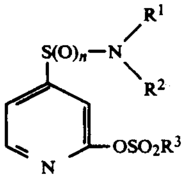

(IB)

Compounds of formula (I) in which X is carbon bearing a hydrogen atom and the groups $R^a$ and $R^b$ occupy 1 and 3 positions relative to each other may be described by Formula (IC):

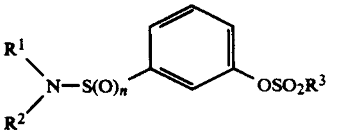

(IC)

Compounds according to Formulae (IA) and (IB) for which the value of n is 2 may be prepared from the corresponding 2-pyridone precursor of formula (IIA) or (IIB):

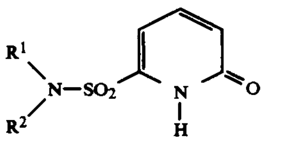

(IIA)

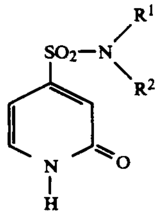

(IIB)

wherein $R^1$ and $R^2$ have any of the meanings given hereinbefore, by reaction of a sulphonyl halide of formula $R^3SO_2$-Hal, wherein $R^3$ has any of the meanings given hereinbefore and Hal represents halogen, for example chlorine, bromine or fluorine, optionally in the presence of a base, for example pyridine or a trialkylamine such as triethylamine, in an inert solvent such as dichloromethane.

The pyridones of formula (IIA) or (IIB) may be prepared from the corresponding 2-halopyridine of formula (IIIA) or (IIIB):

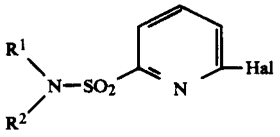

(IIIA)

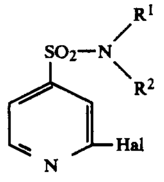

(IIIB)

wherein $R^1$ and $R^2$ have any of the meanings given hereinbefore and Hal is halogen, for example chlorine, bromine or fluorine, by a two stage process. Firstly, the halogen substituent is displaced by a benzyloxy group to give the corresponding 2-benzyloxypyridine of formula (IVA) or (IVB):

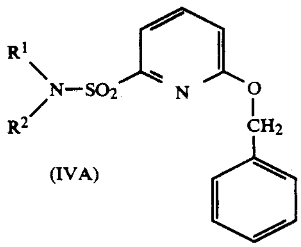

(IVA)

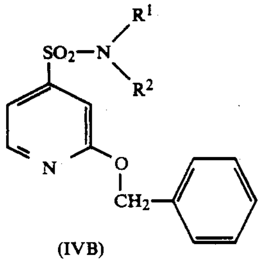

(IVB)

Although an unsubstituted benzyloxy group is favoured for this reaction stage, any benzyl group having a simple ring substituent which is inert to the reaction conditions may also be employed. The displacement may be conveniently performed by reaction with benzyl alcohol in the presence of a base, for example sodium hydride, in an inert solvent such as tetrahydrofuran or dimethylformamide. Debenzylation of the compound of formula (IVA) or (IVB) then gives the corresponding 2-pyridone of formula (IIA) or (IIB). Debenzylation may be conveniently performed under acidic conditions, for example by heating the compound of formula (IVA) or (IVB) in the presence of a mixture of acetic acid and concentrated aqueous hydrobromic acid, or by heating the compound of formula (IVA) or (IVB) in the presence of trifluoroacetic acid in an inert solvent. Debenzylation may also be performed by hydrogenolysis, for example by catalytic hydrogenation.

The 2-pyridones of formula (IIA) and (IIB) may also be prepared from the corresponding 1-halopyridines of formula (IIIA) or (IIIB) directly by acid or base catalysed hydrolysis.

Those skilled in the art will recognise that the 2-pyridones of formula (IIA) and (IIB) exist in tautomeric equilibrium with the corresponding 2-hydroxypyridines.

The compounds of formula (IIIA) and (IIIB) may be prepared from 2,6- and 2,4-dihalopyridines respectively by the following sequence of processes. A 2,6-dihalopyridine, of formula (VA) or a 2,4-dihalopyridine of formula (VB):

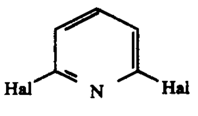

(VA)

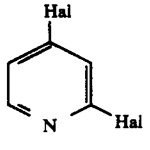

(VB)

wherein Hal represents a halogen, for example chlorine, bromine or fluorine, is reacted with one molar equivalent of benzylthiol or a simple derivative thereof having a ring substituent which is inert to the reaction conditions, in the presence of a base, for example sodium hydride; the reaction may be carried out in any suitable inert solvent such as tetrahydrofuran and produces the corresponding 2-halo-6-benzylthiopyridine or a 2-halo-4-benzylthiopyridine of formula (VIA) or (VIB):

(VIA)

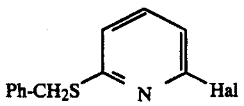

(VIB)

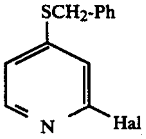

wherein Hal represents a halogen, for example chlorine, bromine or fluorine, and Ph represents phenyl or a simple ring-substituted derivative thereof as described above. The specific 2-halo-4-benzyl substitution pattern of the compounds of formula (VIB) obtained by this process has been confirmed by spectrometric analysis. The compounds of formula (VIA) or (VIB) may then be subjected to oxidative debenzylation, for example by reaction with chlorine in the presence of water optionally in the presence of a solvent, to give the corresponding 2-halopyridine-6-sulphonyl chloride or 2-halopyridine-4-sulphonyl chloride of formula (VIIA) or (VIIB):

(VIIA)

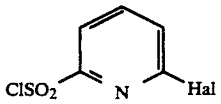

(VIIB)

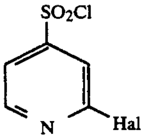

The compound of formula (VIIA) or (VIIB) may then be reacted either with one equivalent of an amine of formula $(R^1)(R^2)NH$ in the presence of an acid scavenger, or with two equivalents of the amine of formula $(R^1)(R^2)NH$, to give the desired compound of formula of formula (IIIA) or (IIIB).

These processes are summarised in Schemes I and II for the particular case of the preparation of compounds of formula (IA) wherein n is 2. The summary applies mutatis mutandis for the preparation of compounds of formula (IB).

SCHEME I

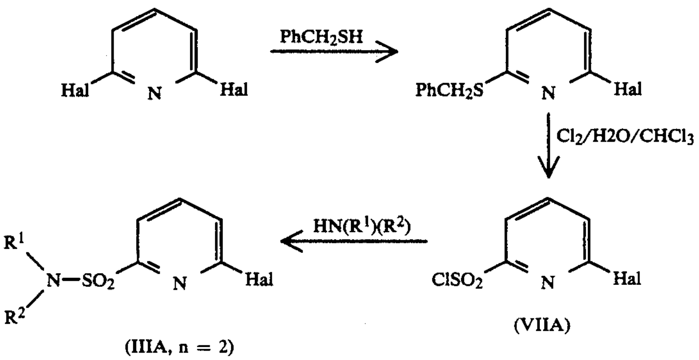

(IIIA, n = 2) (VIIA)

Key: Ph = phenyl

SCHEME II

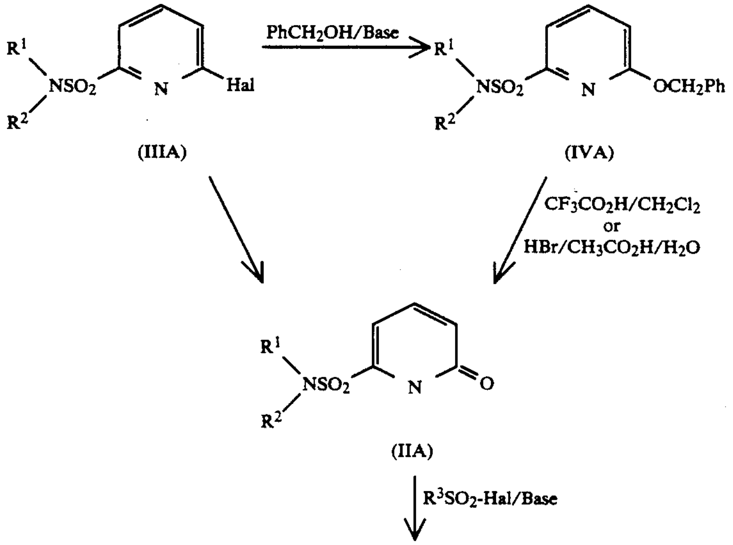

(IIIA) (IVA) (IIA)

-continued

SCHEME II

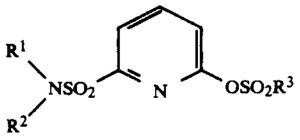

(IA)

Key: Ph = Phenyl

Compounds of formula (IA) having a lower oxidation state (i.e. for which the value of n is 0 or 1) may be prepared from 2,6-dihydroxypyridine by the following sequence of processes. The dihydroxypyridine is reacted with two molar equivalents of a sulphonyl halide of formula $R^3SO_2$-Hal, wherein $R^3$ has any of the meanings given hereinbefore and Hal represents halogen, for example chlorine or bromine. The reaction may be carried out in the presence of a base such as pyridine or a trialkylamine, for example triethylamine or trimethylamine, in a suitable inert solvent such as dichloromethane, to give the corresponding 2,6-bis sulphonate of formula (VIIIA). Reaction of this product with one molar equivalent of benzenethiol or a simple derivative thereof in the presence of a base in an inert solvent then gives the corresponding compound of formula (IXA):

(VIIIA)

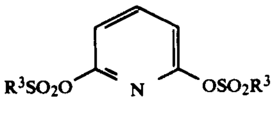

-continued (IXA)

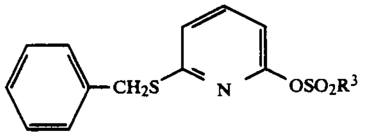

Debenzylation of the compound of formula (IXA) by reaction with sulphuryl chloride in an inert solvent produces an intermediate sulphenyl chloride which may be reacted with an amine of formula $(R^1)(R^2)NH$, wherein $R^1$ and $R^2$ have any of the meanings given hereinbefore, to give the corresponding product of formula (IA) for which n is 0. The corresponding compound of formula (IA) for which n is 1 may be obtained by controlled oxidation of this product, for example by reaction with meta-chloroperbenzoic acid. These processes are summarised in Scheme III.

SCHEME III

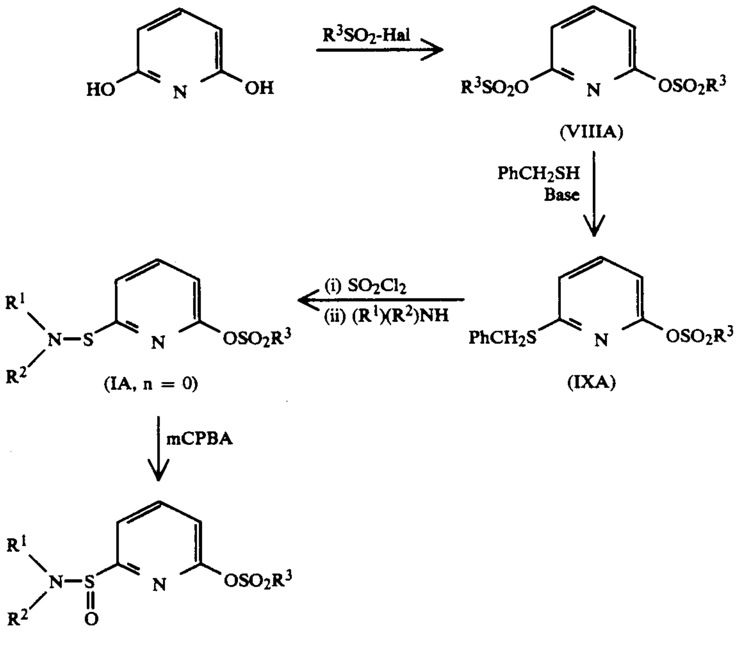

(IA, n = 1)

Key:
Ph = Phenyl
mCPBA = m-chloroperbenzoic acid.

Compounds of formula (IC) wherein $R^1$, $R^2$ and $R^3$ have any of the meanings given hereinbefore and wherein n is 2 may be prepared from 3-benzoyloxybenzenesulphonyl chloride by the following sequence of processes. 3-benzoyloxybenzenesulphonyl chloride may be reacted with an amine of formula $(R^1)(R^2)NH$, either in the presence of an acid scavenger, for example pyridine or a trialkylamine such as triethylamine, or in the presence of excess of the amine of formula $(R^1)(R^2)NH$, to give the corresponding compound of formula (X):

(X)

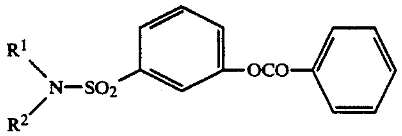

Basic hydrolysis of the compound of formula (X), for example by reaction with an alkali metal hydroxide such as sodium hydroxide in a suitable solvent such as tetrahydrofuran gives the corresponding 3-hydroxybenzenesulphonamide of formula (XI):

(XI)

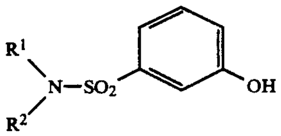

which may be reacted with a sulphonyl halide of formula $R^3SO_2$-Hal, wherein $R^3$ has any of the meanings given hereinbefore and Hal is a halogen atom, for example chlorine or bromine, to give the desired compound of formula (IC). These processes are summarised in Scheme IV. The preparation of 3-benzoyloxybenzenesulphonyl chloride is described in by Kato et al in The Journal of Pesticide Science, Volume 13, pp 107-115 (1988).

SCHEME V

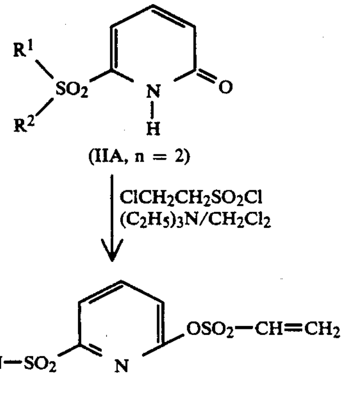

All of the processes described herein may be carried out using alternative solvents or diluents and may be accelerated or lead to higher yields of product when performed at elevated temperatures or in the presence of appropriate catalysts. Further details of many of the processes described herein may be found in the Examples.

Many of the intermediates described herein are believed to be novel. In a further aspect, therefore, the invention provides the following:

a compound of formula (II):

(II)

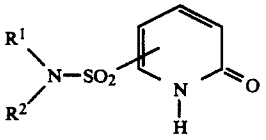

SCHEME IV

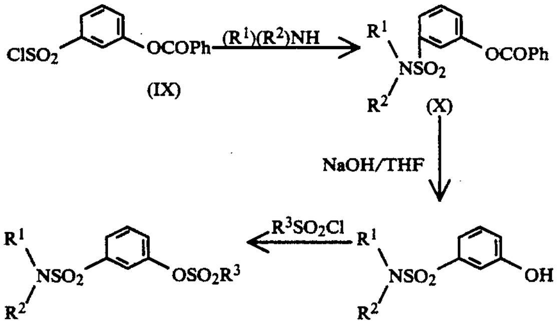

Key: THF = Tetrahydrofuran
Ph = Phenyl

Individual variants of the general processes described herein may be necessary in specific cases where the nature of the substituents may give rise to the possibility of competing reactions. By way of example, a specific variant of the processes described, particularly suitable for the preparation of compounds of formula (I) wherein $R^3$ is ethenyl is summarised in Scheme V. Other variants of the general processes described herein are described in the Examples.

wherein $R^1$ and $R^2$ have any of the values given hereinbefore and the group $(R^1)(R^2)NSO_2$ is in the 4 or the 6 position relative to the ring nitrogen atom;

a compound of formula (III):

(III)

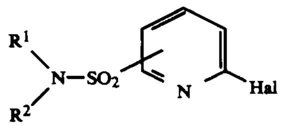

wherein Hal is a halogen atom, and $R^1$ and $R^2$ have any of the values given hereinbefore, and the group $(R^1)(R^2)NSO_2$ is in the 4 or the 6 position relative to the ring nitrogen atom;

a compound of formula (IV):

(IV)

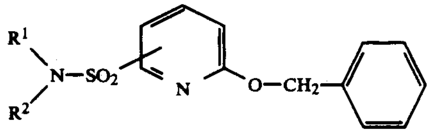

wherein $R^1$ and $R^2$ have any of the values given hereinbefore and the group $(R^1)(R^2)NSO_2$ is in the 4 or the 6 position relative to the ring nitrogen atom;

a compound of formula (X):

(X)

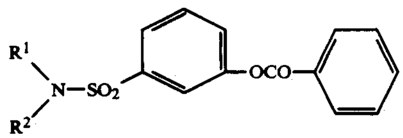

wherein $R^1$ and $R^2$ have any of the values given hereinbefore; and a compound of formula (XI):

(XI)

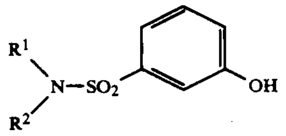

wherein $R^1$ and $R^2$ have any of the values given hereinbefore.

The compounds of formula (I) may be used to combat and control infestations of insect pests. The insect pests which may be combated and controlled by the use of the invention compounds include those pests associated with agriculture (which term includes the growing of crops for food and fibre products, horticulture and animal husbandry), forestry, the storage of products of vegetable origin, such as fruit grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compounds of the invention or complement the activity, for example by increasing the speed of effect, improving kill or knockdown of target insect pests, or overcoming repellency. Additionally, multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

(a) natural pyrethrins or pyrethroids such as permethrin, fenvalerate, deltamethrin, cyhalothrin, biphenthrin, fenpropathrin, cyfluthrin, tefluthrin, empenthrin, ethofenprox, tetramethrin, bioallethrin, fenfluthrin, prallethrin, 5-benzyl-3-furylmethyl (E)-(1R,3S)-2,2-dimethyl-3-(2-oxothiolan-3-ylidenemethyl)cyclopropane carboxylate and pentafluorobenzyl (cis)-3-[2-fluoro-2-(methoxycarbonyl)ethenyl]-2,2-dimethylcyclopropane carboxylate;

(b) organophosphates such as profenofos, sulprofos, dichlorvos, methyl parathion, azinphos-methyl, demeton-s-methyl, heptenophos, thiometon, fenamiphos, monocrotophos, triazophos, methamidophos, dimethoate, phosphamidon, malathion, chlorpyrifos, phosalone, fensulphothion, fonofos, phorate, phoxim, pyrimiphos-methyl, fenitrothion and diazinon;

(c) carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) benzoyl ureas such as triflumuron and chlorofluazuron;

(e) organic tin compounds such as cyhexatin, fenbutatin oxide and azocyclotin;

(f) macrolides such as avermectins or milbemycins, for example abamectin, avermectin and milbemycin;

(g) hormones and synthetic mimics thereof such as juvenile hormone, juvabione, ecdysones, methoprene and hydroprene;

(h) pheromones;

(i) organochlorine compounds such as benzene hexachloride, DDT, chlordane, dieldrin and endosulfan.

In addition to the major chemical classes of insecticide listed above, other insecticides having particular targets may be employed in the mixture if appropriate for the intended utility of the mixture. For instance selective insecticides for particular crops, for example stem borer specific insecticides for use in rice such as cartap or buprofezin, can be employed. Alternatively, insecticides or acaricides specific for the control of specific insect growth stages, for example ovolarvicides such as clofentezine, amitraz, chlordimeform, flubenzimine, hexythiazox and tetradifon; motilicides such as dicofol or propargite; adulticides such as bromopropylate, chlorobenzilate; or insect growth regulators such as hydramethylnon, cyromazine, methoprene, chlorfluazuron and diflubenzuron may also be included in the compositions.

Examples of suitable insecticide synergists for use in the compositions include piperonyl butoxide, sesamex and dodecyl imidazole.

Suitable herbicides, fungicides and plant growth regulators for inclusion in the compositions will depend upon the intended target and the effect required. An example of a rice-selective herbicide which can be included is propanil; an example of a plant growth regulator for use in cotton is "Pix"; and examples of fungicides for use in rice include blasticides such as blasticidin-S. The choice of other ingredients to be used in admixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pest to be controlled, and the effects required of the mixture. However, in general, the additional active ingredient of the composition will be applied at about the rate at which it would be applied on its own, or at a lower rate if synergy occurs.

The compositions may be in the form of dusting powders wherein the active ingredient is mixed with a solid diluent or carrier, for example kaolin, bentonite, kieselguhr or talc, or they may be in the form of granules wherein the active ingredient is absorbed in a porous granular material, for example pumice.

Alternatively, the compositions may be in the form of liquid preparations to be used as dips, sprays or aerosols. Dips and sprays are generally aqueous dispersions or emulsions of the active ingredient in the presence of one or more known wetting agents (surface active agents). Aerosol compositions may contain the active ingredient or ingredients, a propellant and an inert diluent, for example odouless kerosene or alkylated benzenes. In a preferred form, aerosol compositions may contain from 0.005% to 4% of active ingredient or ingredients, the remainder of the composition comprising a solvent, selected from odorless kerosene and alkylated benzenes, and a propellant. Aerosol compositions may optionally incorporate other additives, for example perfumes or corrosion inhibitors.

Wetting agents, dispersing agents and emulsifying agents may be of the cationic, anionic or non-ionic type. Suitable agents of the cationic type include, for example, quaternary ammonium compounds, for example cetyltrimethylammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium lignosulphonate, calcium lignosulphonate, ammonium lignosulphonate, butylnaphthalenesulphonate and a mixture of the sodium salts of diisopropyl- and triisopropyl naphthalenesulphonates. Suitable agents of the non-ionic tyoe include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a sutiable solvent, for example a ketonic solvent such as diacetone alcohol, or an aromatic solvent such as trimethylbenzene, and optionally adding the mixture so obtained to water which may contain one or more known wetting, dispersing or emulsifying agents.

Other suitable organic solvents are dimethylformamide, ethylene dichloride, isopropyl alcohol, propylene glycol and other glycols, diacetone alcohol, toluene, kerosene, white oil, methylnaphthalene, xylenes, trichloroethylene, N-methyl-2-pyrollidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and, after such storage, to be capable of dilution with water to form aqueous preparations which remain homogeneous for a sufficient time to enable them to be applied by conventional spray equipment. The concentrates may contain 1–99% by weight of the active ingredient or ingredients. When diluted to form aqueous preparations, such preparations may contain varying amounts of the active ingredient depending upon the purpose for which they are to be used. For agricultural or horticultural purposes, an aqueous preparation containing between 0.0001% and 0.1% by weight of the active ingredient or ingredients is particularly useful. In use, the compositions are applied to the pests, to the locus of the pests, to the habitat of the pests, or to growing plants liable to infestation by the pests, by any of the known means of applying pesticidal compositions, for example by dusting or spraying or in a granular formulation.

The compounds of formula (I) and compositions comprising them are very toxic to a variety of insect, and other invertebrate pests, including, for example, the following:

*Myzus persicae* (aphid)
*Aphis gossypii* (aphid)
*Aphis fabae* (aphid)
*Megoura viceae* (aphid)
*Plutella maculipennis* (diamond back moth)
*Spodoptera littoralis* (cotton leafworm)
*Heliothis virescens* (tobacco budworm)
Diabrotica spp. (rootworms)
Agrotis spp. (cutworms)
*Chilo partellus* (maize stem borer)
*Nilaparvata lugens* (planthopper)
*Nephotettix cincticeps* (leafhopper)

The compounds of formula (I) are particularly effective for the control pests of hopper pests such as planthoppers (Delphacidae), for example Nilaparvata spp., and leafhoppers (Cicadellidae), for example Nephotettix spp. They are also effective against soil pests such as Diabrotica spp. and sucking pests such as aphids, for example Myzus spp., Aphis spp. or Megoura spp. The compounds are characterised by a particularly high level of systemic activity.

The following Examples illustrate various aspects of this invention. In the preparation Examples the products were usually identified and characterised by means of nuclear magnetic resonance (NMR) spectroscopy and infra red (IR) spectroscopy. In each case where a product is specifically named its spectral characteristics are consistent with the assigned structure.

In the Examples, gas liquid chromatography (GLC) retention times were determined on a Hewlett Packard 5890 Gas Chromatograph, using a Chrompak C.P. Sil 5 C.B. column of 12.5 m length and 0.2 mm internal diameter. Unless otherwise stated, the injection temperature was 100° C., and a temperature gradient of 15° C. per minute employed, up to a maximum temperature of 280° C., maintained for 4 minutes. The carrier gas was helium at a column head pressure maintained at 11 psi. Alternative injection and maximum temperatures are indicated in the Examples where appropriate.

$^1$H NMR spectrometry was performed at a frequency of 270 MHz on a Jeol FX 270 NMR spectrometry unless otherwise indicated. 90 Mhz, 60 Mhz and 400 MHz $^1$H NMR spectrometry were performed using Jeol FX 90Q, Jeol PMX 60 SI and Jeol GX 400 spectrometers. $^{19}$F NMR spectrometry was performed using a Jeol FX 90Q spectrometer at a frequency of 84.26 MHz. All NMR shift values ( ) are quoted in ppm relative to a standard (TMS or $CFCl_3$). In the NMR data, the following abbreviations are used: s=singlet, d=doublet, t=triplet, q=quartet, dd=double doublet, m=multiplet, b=broad.

Molecular ion (M+) peaks were determined on one of three mass spectrometers: Jeol DX 303, Kratos MS 80 or Hewlett Packard HP 5992.

EXAMPLE 1

This Example illustrates the stages in the preparation of 2-[N-(prop-2-yl)sulphamoyl]-6-(methanesulphonyloxy)pyridine (compound No. 1)

(i) 2-benzylthio-6-fluoropyridine.

A solution of benzylthiol (5.4 g) in tetrahydrofuran (25 $cm^3$) was added dropwise to a stirred suspension of sodium hydride (1.9 g of a 55% of a dispersion in oil) in tetrahydrofuran (350 $cm^3$) under a nitrogen atmosphere. The mixture was stirred for 30 minutes and a solution of 2,6-difluoropyridine (5 g) in tetrahydrofuran (25 $cm^3$) was added dropwise. The mixture was stirred for a further 3 hours and then carefully quenched with water. The products were extracted into diethyl ether and the combined ether extracts were washed with water and brine solution, then dried over anhydrous magnesium sulphate, filtered and concentrated by evaporation under reduced pressure. The residual dark liquid was purified by chromatography on a silica gel support, eluting with hexane containing 5% by volume ethyl acetate. Fractions containing 15–20 $cm^3$ of eluent were collected separately during the elution, the product being collected in fractions 11 to 19. Evaporation of the eluent gave the title product (7.1 g) as a clear liquid.

$^1$H NMR ($CDCl_3$): 4.40 (2H,s); 6.57 (1H,dd); 7.02 (1H,dd); 7.2–7.6 (6H,m).

(ii) 6-fluoropyridine-2-sulphonyl chloride.

Chlorine gas was bubbled through a vigorously stirred mixture of chloroform (20 $cm^3$), water (20 $cm^3$) and 2-benzylthio-6-fluoropyridine (1 g) for a total of 95 minutes. Aqueous sodium metabisulphite solution was added to the mixture and the chloroform layer was separated. The aqueous layer was extracted with further chloroform and the combined chloroform layers were washed with water, dried over anhydrous magnesium sulphate, filtered and concentrated by evaporation under reduced pressure to yield a residual oil (2.0 g) which was used without further purification.

(iii) 2-[N-(prop-2-yl)sulphamoyl]-6-fluoropyridine.

A mixture of 6-fluoropyridine-2-sulphonyl chloride (in the form of the oil obtained in Example 2; 1.0 g) 2-aminopropane (0.6 g, 2 equivalents) and chloroform (10 $cm^3$) was stirred for 1 hour, then poured into water. The organic layer was separated, dried over anhydrous magnesium sulphate and concentrated by evaporation under reduced pressure to give a green liquid which crystallised on standing. Purification by chromatography on a silica gel support, eluting with hexane containing 30% by volume ethyl acetate gave the title product (0.385 g) as a light brown solid which could be further purified by recrystallisation from a hexane/ethyl acetate mixture.

Melting Point: 105°–105.7° C.

$^1$H NMR ($CDCl_3$): 1.16 (6H,d); ca3.6 (1H,m), ca4.8 (1H,bd); 7.15 (1H,m); 6.9–7.2 (2H,m)

(iv) 2-[N-(prop-2-yl)sulphamoyl]-6-(benzlyoxy)pyridine.

A solution of benzyl alcohol (0.141 g) in tetrahydrofuran (5 $cm^3$) was added dropwise to a stirred suspension of sodium hydride (0.57 g of a 55% suspension in oil) in tetrahydrofuran (20 $cm^3$). The mixture was stirred for 30 minutes and a solution of 2-[N-(prop-2-yl)]-6-fluoropyridine (0.285 g) was added dropwise at the ambient temperature (ca 22° C.). The mixture was stirred for 2 hours at the ambient temperature after which time analysis by thin layer chromatography showed no reaction. The mixture was heated to 60° C. and stirring continued for a further 75 minutes. No reaction was detected, and further 15 tetrahydrofuran (15 $cm^3$) and sodium hydride (0.5 g of a 55% dispersion in oil) were added and stirring continued at 60° C. for a further 90 minutes*. The mixture was then allowed to cool to the ambient temperature and was allowed to stand overnight. The mixture was poured onto water and extracted twice with diethyl ether. The combined organic layers were washed with water and the washings extracted with further diethyl ether. The combined organic layers were dried over anhydrous magnesium sulphate, filtered and concentrated by evaporation of the solvent under reduced pressure to leave a clear brown liquid which was purified by column chromatography on a silica gel support, eluting with hexane containing 20% ethyl acetate to give the title product (0.26 g) as a crystalline solid which could be further purified by recrystallisation from a hexane/ethyl acetate mixture.

Melting Point: 105.5°–107° C.

400 MHz $^1$H NMR ($CDCl_3$): 1.0 (6H,d); 3.5 (1H,m); 4.55 (1H,bd); 5.42 (2H,s); 6.98 (1H,d); 7.3–7.5 (5H,m); 7.6 (1H,d); 7.75 (1H,dd)

* Footnote: In the following Examples this stage was modified according to the progress of the reaction as monitored by gas and thin layer chromatography. Where reaction rates were found to be slow additional base, or preferably additional benzoxide, was added to the reaction mixture. Dimethylformamide was found to be suitable as an alternative solvent and frequently led to an increased reaction rate.

(v) 2-[N-(prop-2-yl)sulphamoyl]pyrid-6-one.

A mixture of 2-[N-(prop-2-yl)sulphamoyl]-6-(benzyloxy)pyridine (0.11 g), 48% aqueous hydrobromic acid solution (1 $cm^3$) and glacial acetic acid (1 $cm^3$) was heated at the reflux temperature for 30 minutes. The mixture was allowed to cool then partitioned between a mixture of water and dichloromethane. The organic layer was separated and the aqueous layer extracted twice with further dichloromethane. The combined organic layers were washed with water and brine, dried over anhydrous magnesium sulphate, filtered and concentrated by evaporation of the solvent under reduced pressure to give a pale yellow oil which was purified by column chromatography on a silica gel support, eluting with hexane to remove impurities and further eluting with ethyl acetate to give the title product as a yellow oil (0.052 g).

400 MHz $^1H$ NMR ($CDCl_3$): 1.15 (6H,d); 3.5 (1H,m); 6.1 (1H,bd); 6.82 (1H,d); 7.09 (1H,d); 7.65 (1H,dd).

(vi) 2-[N-(prop-2-yl)sulphamoyl]-6-(methanesulphonyloxy)pyridine (compound No 1)

2-[(N-prop-2-yl)sulphamoyl]pyrid-6-one (0.052 g) was dissolved in dichloromethane (4 $cm^3$). Methane sulphonylchloride (0.027 g) was added dropwise in dichloromethane (1 $cm^3$) and the reaction mixture was stirred for 45 minutes. Triethylamine (0.024 g) in dichloromethane (1 $cm^3$) was added dropwise and the reaction mixture was stirred for 2 hours. The mixture was left overnight and then refluxed for 2 hours. The cooled reaction mixture was poured into water and the product extracted into dichloromethane twice. The dichloromethane extracts were combined, dried, and evaporated under reduced pressure to leave the crude product.

The crude reaction product was purified by column chromatography on a silica gel support, eluting with hexane containing 30% by volume ethyl acetate to give the title product as a white solid (0.07 g).

$^1H$ NMR ($CDCl_3$): 1.14 (6H,d); 3.55 (3H,s); 3.6 (1H,m); 4.75 (1H,bd); 7.3 (1H,d); 8.0 (2H,m)

Examples 2–49 illustrate the preparation of further examples according to the invention using essentially the same procedures as those described in stages (i)–(vi) of Example 1. In each example, characteristic data are given for final products and for intermediates which have not been described in earlier examples. In some cases, intermediates were not isolated, or were used without purification, and no data were recorded. Individual reaction conditions employed may have differed from those described in Example 1 according to requirements for optimisation of the reaction. Such requirements were determined by monitoring of the reaction by gas or thin layer chromatography and the optimisation techniques which were employed were within the normal skill of the chemist. Intermediates are identified by name and by the reaction stage number [(i)–(vi)] corresponding to the method of their preparation by reference to Example 1. Where alternative processes were used, these are fully described in the Example.

EXAMPLE 2

2-[N-methyl-N-(prop-2-yl)sulphamoyl]-6-(methanesulphonyloxy)pyridine (compound No. 2).

Melting Point: 69.4°–70.7° C.

$^1H$ NMR ($CDCl_3$): 1.04 (6H,d); 2.91 (3H,s); 3.57 (3H,s); 4.23 (1H,m); 7.26 (1H,d); 7.9 (1H,d); 8.03 (1H, t).

(iii) 2-[N-methyl-N-(prop-2-yl)sulphamoyl]-6-fluoropyridine.

$^1H$ NMR ($CDCl_3$): 1.12 (6H,d); 2.88 (3H,s); 4.30 (1H,m); 7.1 (1H,d); 7.84 (1H,d); 7.98 (1H,q).

(iv) 2-[N-methyl-N-(prop-2-yl)sulphamoyl]-6-(benzyloxy)pyridine.

$^1H$ ($CDCl_3$): 1.0 (6H,d); 2.84 (3H,s); 4.26 (1H,m); 5.42 (2H,s); 6.97 (1H,d); 7.3–7.5 (5H,m); 7.58 (1H,d); 7.75 (1H,dd).

(v) 2-[N-methyl-N-(prop-2-yl)-sulphamoyl]-pyrid-6-one.

EXAMPLE 3

2-[N-cyclopropylsulphamoyl]-6-(methanesulphonyloxy)pyridine (compound No. 3).

$^1H$ NMR ($CDCl_3$) 0.68 (4H,m); 2.42 (1H,m); 3.55 (3H,s); 5.22 (1H,bs); 7.3 (1H,d); 8.05 (2H,m).

(iii) 2-[N-cyclopropyl sulphamoyl ]-6-fluoropyridine $^1H$ NMR ($CDCl_3$): 0.7 (4H,m); 2.36 (1H,m); 5.4 (1H,bs); 7.18 (1H,dd); 8.00 (1H,dd); 8.05 (1H,dd)

(iv) 2-[N-cyclopropylsulphamoyl]-6-(benzyloxy)pyridine.

$^1H$ NMR ($CDCl_3$): 0.55 (4H,m); 2.08 (1H,m); 5.07 (1H,bs); 5.42 (2H,s); 7.01 (1H,d); 7.40 (5H,m); 7.65 (1H,d); 7.8 (1H,t).

(v) 2-[N-cyclopropylsulphamoyl]-pyrid-6-one.

$^1H$ NMR ($CDCl_3$): 0.65 (4H,m); 2.35 (1H,m); 6.40 (1H,bs); 6.85 (1H,d); 7.18 (1H,d); 7.68 (1H,t).

EXAMPLE 4

2-[N-(prop-2-yl)-N-methylsulphamoyl]-6-(4-methylbenzenesulphonyloxy)pyridine (compound No 4).

$^1H$ NMR ($CDCl_3$): 1.00 (6H,d); 2.45 (3H,s); 2.75 (3H,s); 4.12 (1H,m); 7.24 (1H,d); 7.4 (2H,d); 7.8 (1H,d); 7.95 (2H,d).

EXAMPLE 5

2-[N-(1,1,1-trifluoroethyl)sulphamoyl]-6-(methanesulphonyloxy)pyridine (compound No 5).

$^1H$ NMR ($CDCl_3$): 3.15 (1H,bs); 3.60 (3H,s); 3.75 (2H,q); 7.38 (1H,d); 7.95 (1H,d); 8.16 (1H,dd).

EXAMPLE 6

2-[N-acetylsulphamoyl]-6-(methanesulphonyloxy)pyridine (Compound No 6).

$^1H$ NMR ($CDCl_3$): 2.05 (3H,s); 3.4 (3H,s); 7.28 (1H,dd); 8.05 (2H,m).

(iii) (Alternative process): 6-fluoro-2-sulphamoylpyridine.

A solution of 6-fluoropyridine-2-sulphonyl chloride (1.2 g) in diethyl ether (100 $cm^3$) was cooled to −60° C. and ammonia was slowly bubbled though the stirred solution. Further 6-fluoropyridine-2-sulphonyl chloride (1 g) was added and the introduction of ammonia continued. The reaction mixture was warmed to the ambient temperature and poured into water, and the product extracted into diethyl ether. The aqueous layer was neutralised with dilute aqueous hydrochloric acid solution and then further extracted with diethyl ether. The combined diethyl ether washings were dried over anhydrous magnesium sulphate, filtered and evaporated to leave the title product.

$^1H$ NMR (DMSO): 7.02 (2H,bs); 7.18 (1H,dd); 7.90 (1H,dd); 8.09 (1H,dd).

(iv) 2-(N-acetylsulphamoyl)-6-benzyloxy-pyridine. 2-Sulphamoyl-6-benzyloxypyridine was prepared using the process of Example 1 (iv):

$^1H$ NMR ($CDCl_3$): 4.80 (2H,bs); 5.40 (2H,s); 7.00 (1H,d); 7.40 (5H,m); 7.60 (1H,d); 7.75 (1H,dd).

This compound was then acetylated using the following procedure:

To 2-[sulphamoyl]-6-benzyloxypyridine (1 g) in solution in dichloromethane (2 $cm^3$) was added acetic anhydride (0.390 g) and 2 drops of concentrated sulphuric acid. The reaction mixture was stirred at the ambient temperature and acetic acid (2 $cm^3$) added. The reaction mixture was heated at the reflux temperature for 2 hours, cooled, and added to water. The product was extracted into ethyl acetate. The combined organic layers were dried over anhydrous nesium sulphate and the solvent evaporated under reduced pressure. The product was purified by silica chromatography eluting with hexane containing a progressively increasing proportion of ethyl acetate (10–60% by volume).

$^1H$ NMR ($CDCl_3$): 2.14 (3H,s); 5.39 (2H,s); 7.06 (1H,d); 7.40 (5H,m); 7.80 (2H,m); 8.35 (1H,bs).

(v) 2-(N-acetylsulphamoyl)pyrid-6-one $^1$H NMR ($CDCl_3$): 2.05 (3H,s); 6.89 (1H,d); 7.4 (1H,s); 7.58 (1H,d); 7.75 (1H,t).

EXAMPLE 7

2-[N-(1-methylhexyl)sulphamoyl]-6-(methanesulphonyloxy)pyridine (Compound No. 7).

$^1$H NMR ($CDCl_3$): 0.85 (3H,t); 1.08 (3H,d); 1.2 (4H,m); 1.45 (2H,m); 3.42 (1H,m); 3.55 (3H,s); 4.68 (1H,d); 7.30 (1H,d); 7.98 (1H,d); 8.05 ( 1H,t).

EXAMPLE 8

2-[N-methoxy-N-methylsulphamoyl]-6-(methanesulphonyloxy)pyridine. (Compound No 8).

$^1$H NMR ($CDCl_3$): 3.10 (3H,s); 3.60 (3H,s); 3.80 (3H,s); 7.36 (1H,d); 8.00 (1H,d); 8.10 (1H,t).

(iii) Alternative Process: 2-[N-methoxy-N-methylsulphamoyl]-6-fluoropyridine.

A solution of 6-fluoropyridine-2-sulphonylchloride (1.96 g) and methoxylamine hydrochloride (1.96 g) in chloroform (40 $cm^3$) was cooled to −78° C. under an atmosphere of nitrogen and a solution of triethylamine (2.03 g) in chloroform (10 $cm^3$) was added with stirring. The reaction mixture was added to water and the product extracted into chloroform. The combined organic layers were dried over magnesium sulphate, filtered and evaporated to give the title product.

(iv) 2-(N-methoxy-N-methylsulphamoyl)-6-benzyloxypyridine (vi) 2-[N-methoxy-N-methylsulphamoyl]pyrid-6-one.

$^1$H NMR ($CDCl_3$): 2.98 (3H,s); 3.81 (3H,s); 6.95 (1H,d); 7.09 (1H,d); 7.68 (1H,dd); 8.0 (1H,bs).

EXAMPLE 9

2-[N-(2-methoxyethyl)sulphamoyl]-6-(methanesulphonyloxy)pyridine. (Compound No 9).

$^1$H NMR ($CDCl_3$): 3.26 (3H,s); 3.31 (2H,t); 3.42 (2H,t); 3.53 (3H,s); 5.15 (1H,bt); 7.30 (1H,d); 7.92 (1H,d); 8.10 (1H,t).

(iii) 2-[N-(2-methoxyethyl)sulphamoyl]-6-fluoropyridine.

$^1$H NMR ($CDCl_3$): 3.30 (3H,s); 3.32 (2H,t); 3.48 (2H,t); 7.15 (1H,dd); 7.90 (1H,dd); 8.02 (1H,dd).

(iv) 2-[N-(2-methoxyethyl)sulphamoyl]-6-benzyloxypyridine.

$^1$H NMR ($CDCl_3$): 3.2 (5H,m); 3.4 (2H,t); 6.55 (1H,t); 6.85 (1H,d); 7.08 (1H,d); 7.62 (1H,dd).

(v) 2-[N-(2-methyloxyethyl)sulphamoyl]pyrid-6-one.

EXAMPLE 10

2-(N-phenylsulphamoyl)-6-(methanesulphonyloxy)-pyridine (Compound No 10).

$^1$H NMR ($CDCl_3$) 3.40 (3H,s); 6.95 (1H, bs); 7.1–7.30 (6H,m); 7.83 (1H,d); 7.95 (1H,t).

(iii) 2-(N-phenylsulphamoyl)-6-fluoropyridine.

$^1$H NMR ($CDCl_3$); 3.68 (1H,bs); 7.1–7.3 (6H,m); 7 80 (1H,dd); 7.92 (1H,dd).

(iv) 2-(N-phenylsulphamoyl)-6-benzyloxypyridine.

$^1$H NMR ($CDCl_3$): 5.35 (2H,s); 6.90 (4H,m); 7.05–7.5 (9H,m); 7.65 (1H,t).

(v) 2-(N-phenylsulphamoyl)pyrid-6-one.

$^1$H NMR ($CDCl_3$): 6.85 (1H,d); 6.95 (1H,d); 7.1–7.3 (5H,m); 7.55 (1H,dd).

EXAMPLE 11

2-[N-(1-methylpropyl)sulphamoyl]-6-sulphonyloxy)-pyridine. (Compound No. 11).

$^1$H NMR ($CDCl_3$): 0.85 (3H,t); 1.1 (3H,d); 1.48 (2H,m); 3.4 (1H,m); 3.56 (3H,s); 4.55 (1H,bd); 7.30 (1H,d); 8.02 (2H,m).

(iii) 2-[N-(1-methylpropyl)sulphamoyl]-6-fluoropyridine.

$^1$H NMR ($CDCl_3$): 0.85 (3H,t); 1.10 (3H,d); 1.48 (2H,m); 3.40 (1H,m); 4.75 (1H,bs); 7.15 (1H,dd); 7.90 (1H,dd); 8.04 (1H,dd).

(iv) 2-[N-(1-methylpropyl)sulphamoyl]-6-benzyloxypyridine.

$^1$H NMR ($CDCl_3$): 0.8 (3H,t); 0.95 (3H,d); 1.38 (2H,m); 3.30 (1H,m); 4.42 (1H,bd); 5.40 (2H,s); 6.95 (1H,d); 7.30–7.45 (5H,m); 7.60 (1H,d); 7.75 (1H,t).

(v) 2-[N-(1-methylpropyl) sulphamoyl]pyrid-6-one.

$^1$H NMR ($CDCl_3$): 0.85 (3H,t); 1.10 (3H,d); 1.48 (2H,m); 3.34 (1H,m); 6.02 (1H,bd); 6.80 (1H,d); 7.08 (1H,d); 7.60 (1H,t).

EXAMPLE 12

2-[N-(1-methylpropyl)sulphamoyl]-6-(ethane sulphonyloxy)pyridine (Compound No 12).

$^1$H NMR ($CDCl_3$): 0.85 (3H,t); 1.10 (3H,d); 1.45 (2H,m); 1.60 (3H,t); 3.40 (1H,m); 3.70 (2H,q); 4.56 (1H,bd); 7.32 (1H,dd); 8.0 (2H,m).

EXAMPLE 13

2-[N-(prop-2-yl)sulphamoyl]-6-(trifluoromethanesulphonyloxy)pyridine (Compound No 13).

$^1$H NMR ($CDCl_3$): 1.18 (6H,d); 3.65 (1H,m); 4.68 (1H,bd); 7.38 (1H,dd); 8.11 (2H,m).

EXAMPLE 14

2-[N-(prop-2-yl)sulphamoyl]-6-(ethanesulphonyloxy)-pyridine (Compound No. 14).

$^1$H NMR ($CDCl_3$): 1.12 (6H,d); 1.60 (3H,t); 3.58 (1H,m); 3.70 (2H,q); 4.82 (1H,bs); 7.31 (1H,d); 7.99 (1H,d); 8.04 (1H,t).

EXAMPLE 15

2-[N-methyl-N-(prop-2-yl)sulphamoyl]-6-(ethanesulphonyloxy)pyridine (Compound No 15).

$^1$H NMR ($CDCl_3$): 0.95 (6H,d); 1.48 (3H,t); 2.80 (3H,s); 3.65 (2H,q); 4.12 (1H,m); 7.20 (1H,d); 7.80 (1H,d); 7.99 (1H,t).

EXAMPLE 16

2-[N-methyl-N-(prop-2-yl)sulphamoyl]-6-(trifluoromethanesulphonyloxy)pyridine. (Compound No. 16).

$^1$H NMR ($CDCl_3$): 1.10 (6H,d); 2.94 (3H,s); 4.22 (1H,m); 7.35 (1H,dd); 8.08 (2H,m).

EXAMPLE 17

2-[N-(prop-2-yl)sulphamoyl]-6-(2,2,2trifluoroethanesulphonyloxy)pyridine (Compound No.17).

$^1$H NMR ($CDCl_3$): 1.10 (6H,d); 3.58 (1H,m); 4.62 (2H,q); 5.1 (1H,bd); 7.32 (1H,d); 8.05 (2H,m).

EXAMPLE 18

2-[N-(prop-2-yl)sulphamoyl]-6-(benzenesulphonyloxy)-pyridine (Compound No. 18).

$^1$H NMR ($CDCl_3$): 1.15 (6H,d); 3.58 (1H,m); 4.76 (1H,bd); 7.40 (1H,d); 7.70–7.90 (3H,m); 8.05 (1H,m); 8.15 (1H,m); 8.20 (2H,d).

EXAMPLE 19

2-[N-(prop-2-yl)sulphamoyl]-6-(2-phenyl)ethanesulphonyloxy] pyridine (Compound No 19).

$^1H$ NMR ($CDCl_3$): 1.08 (6H,d); 3.32 (2H,m); 3.58 (1H,m); 3.95 (2H,m); 4.6 (1H,bd); 7.2–7.4 (6H,m); 8.0 (2H,m).

EXAMPLE 20

2-[N-(prop-2-yl)sulphamoyl]-6-(propanesulphonyloxy)-pyridine (Compound No 20).

$^1H$ NMR ($CDCl_3$): 1.15 (9H,m); 2.05 (2H,m); 3.60 (1H,m); 3.68 (2H,m); 4.85 (1H,d); 7.30 (1H,d); 8.04 (2H,m).

EXAMPLE 21

2-[N-(prop-2-yl)sulphamoyl]-6-(perfluorohexanesulphonyloxy)pyridine (Compound No. 21).

$^1H$ NMR ($CDCl_3$): 1.17 (6H,d); 3.65 (1H,m); 4.7 (1H,bd); 7.38 (1H,dd); 8.12 (2H,m).

EXAMPLE 22

2[N-(Prop-2-yl)sulphamoyl]-6-butanesulphonyloxy)-pyridine (Compound No. 22).

$^1H$ NMR ($CDCl_3$): 1.00 (3H,t); 1.15 (6H,d); 1.55 (2H,m); 2.00 (2H,m); 3.60 (1H, m); 3.68 (2H,m); 4.68 (1H,bd); 7.30 (1H,d); 8.02 (2H,m).

EXAMPLE 23

2-[N-(Prop-2-yl)sulphamoyl]-6-[4-(trifluoromethyl)benzenesulphonyloxy]pyridine (Compound No. 23).

$^1H$ NMR ($CDCl_3$): 1.0 (6H,d); 3.48 (1H,m); 4.4 (1H,bd); 7.29 (1H,d); 7.9 (4H,dd); 0.04 (1H,t); 8.30 (1H,d).

EXAMPLE 24

2-[N-(prop-2-yl)-sulphamoyl]-6-[4-methoxybenzenesulphonyloxy]pyridine (Compound No. 24).

$^1H$ NMR ($CDCl_3$): 1.04 (6H,d); 3.48 (1H,m); 3.90 (3H,s); 4.5 (1H,bd); 7.05 (2H,m); 7.25 (1H,d); 7.89 (1H,d); 8.00 (3H,m).

EXAMPLE 25

2-[N-(Prop-2-yl)sulphamoyl]-6-[2-thiophenesulphonyloxy]pyridine (Compound No. 25).

$^1H$ NMR ($CDCl_3$): 1.10 (6H,d); 3.53 (1H,m); 4.70 (1H,bd); 7.19 (1H,m); 7.28 (1H,d); 7.80 (1H,dd); 7.98 (3H,m).

EXAMPLE 26

2-[N-(Prop-2-yl)sulphamoyl]-6-(chloromethanesulphonyloxy)pyridine (Compound No. 26).

$^1H$ NMR ($CDCl_3$): 1.12 (6H,d); 3.60 (1H,m); 4.8 (1H,bd); 5.22 (2H,s); 7.35 (1H,d); 8.02 (1H,d); 8.10 (1H,t).

EXAMPLE 27

2-[N-(Prop-2-yl)sulphamoyl]-6-(3-chloropropanesulphonyloxy)pyridine (Compound No. 27).

$^1H$ NMR ($CDCl_3$): 1.14 (6H,d); 2.51 (2H,m); 3.60 (1H,m); 3.80 (2H,t); 3.90 (2H,t); 4.75 (1H,bd); 7.31 (1H,bd); 8.01 (1H,bd); 8.05 (1H,t).

EXAMPLE 28

2-[N-(Prop-2-yl)sulphamoyl]-6-[6-fluoro-2-pyridinesulphonyloxy]pyridine (Compound No. 28).

$^1H$ NMR ($CDCl_3$): 1.02 (6H,d); 3.4 (1H,m); 7.15 (1H,d); 7.4 (2H,m); 7.9 (1H,d); 8.10 (1H,t); 8.20 (2H,m).

EXAMPLE 29

2-[N-(prop-2-yl)sulphamoyl]-6-[2-phenylethylenesulphonyloxy]pyridine (Compound No. 29).

$^1H$ NMR ($CDCl_3$): 1.05 (6H,d); 3.56 (1H,m); 4.55 (1H,bd); 7.25–7.35 (2H,m); 7.36 (3H,m); 7.60 (2H,m); 7.80 (1H,d); 7.91 (1H,bd); 8.03 (1H,t).

EXAMPLE 30

2-[N-(Prop-2-yl)sulphamoyl]-6-(dichloromethanesulphonyloxy)pyridine (Compound No. 30).

$^1H$ NMR ($CDCl_3$): 1.15 (6H,d); 3.58 (1H,m); 5.37 (1H,bd); 7.34 (1H,s); 7.36 (1H,d); 8.05 (1H,bd); 8.12 (1H,t).

EXAMPLE 31

2-[N-cyclopropylsulphamoyl]-6-(ethanesulphonyloxy)-pyridine (Compound No. 31).

$^1H$ NMR ($CDCl_3$): 0.7 (4H,m); 1.6 (3H,t); 2.45 (1H,m); 3.7 (2H,q); 5.15 (1H,bs); 7.35 (2H,bd); 8.05 (2H,m).

EXAMPLE 32

2-[Sulphamoyl]-6-(methanesulphonyloxy)pyridine (Compound No. 32).

$^1H$ NMR (DMSO): 3.68 (3H,s); 7.5 (1H,d); 7.68 (2H,bs); 7.9 (1H,d); 8.2 (1H,dd).

EXAMPLE 33

2-[N-prop-2-yl]-6-(ethylenesulphonyloxy)pyridine (Compound No. 33).

Alternative process: To a stirred solution of 2-[N-prop-2-yl]pyrid-6-one (0.5g) and 2-chloroethanesulphonyl chloride (0.385g) in dichloromethane (10 $cm^3$) at 0° C. was added a solution of triethylamine (0.33 g) in dichloromethane (5 $cm^3$). The reaction mixture was poured onto water and the product extracted into dichloromethane. The combined organic layers were dried over magnesium sulphate, filtered and the solvent removed by evaporation under reduced pressure. The resulting crude product was purified by silica chromatography eluting with hexane containing 20% by volume ethyl acetate.

$^1H$ NMR ($CDCl_3$): 1.15 (6H,d); 3.6 (1H,m); 4.8 (1H,d); 6.3 (1H,d); 6.6 (1H,d); 7.2 (1H,dd); 7.3 (1H,d); 7.95 (1H,d); 8.05 (1H,t).

EXAMPLE 34

2-[N,N-di-(prop-2-yl)sulphamoyl]-6-(methanesulphonyloxy)pyridine (Compound No. 34).

$^1H$ NMR ($CDCl_3$): 1.30 (12H,d); 3.54 (3H,s); 3.90 (2H,m); 7.25 (1H,dd); 8.00 (2H,m);

(iii) 2-[N-di-(prop-2-yl)sulphamoyl]-6-fluoropyridine.

Note: Since the reaction to form this product was slow, the reaction mixture was warmed to room temperature and two equivalents of pyridine were added.

$^1H$ NMR: ($CDCl_3$): 1.30 (12H,d); 3.95 (2H,m); 7.08 (1H,dd); 7.88 (1H,dd); 7.95 (1H,dd).

(v) 2-[N,N-di-(prop-2-yl)sulphamoyl]pyrid-6-one $^1H$ NMR ($CDCl_3$): 1.30 (12H,d); 3.80 (2H,m); 6.75 (1H,d); 6.95 (1H,d); 7.55 (1H,dd).

EXAMPLE 35

2-[N-(cyclopropyl)methyl-N-methyl]-6-(methanesulphonyloxy)pyridine (Compound No. 35).

$^1H$ NMR ($CDCl_3$): 0.20 (2H,m); 0.55 (2H,m); 0.95 (1H,m); 3.05 (3H,s); 3.13 (2H,d); 3.55 (3H,s); 7.25 (1H,d); 7.90 (1H,d); 8.0 (1H,t).

(iii) 2-[N-(cyclopropyl)methyl-N-methyl]-6-fluoropyridine (A) 2-[N-(cyclopropyl)methyl-N-methyl]-6-fluoropyridine was prepared by the N-methylation of 2-[-N-(cyclopropyl)methyl]-6-fluoropyridine (B) which was prepared according to the method of Example 1 (iii).

$^1$H NMR ($CDCl_3$): (B): 0.20 (2H,m); 0.50 (2H,m); 0.95 (1H,m); 3.05 (2H,t); 4.90 (1H,bt); 7.18 (1H,dd); 7.90 (1H,dd); 8.05 (1H,dd).

Compound (B) was methylated using dimethyl sulphate under standard conditions to produce compound (A).

$^1$H NMR ($CDCl_3$): 0.20 (2H,m); 0.50 (2H,m); 0.95 (1H,m); 3.00 (3H,s); 3.15 (2H,d); 7.10 (1H,dd); 7.80 (1H,dd); 8.00 (1H,dd).

(iv) 2-[N-(cyclopropyl)methyl-N-methylsulphamoyl]-6-(benzyloxy)pyridine.

$^1$H NMR ($CDCl_3$): 0.20 (2H,m); 0.50 (2H,m); 0.95 (1H,m); 3.00 (1H,s); 3.10 (2H,d); 5.45 (2H,s); 7.0 (1H,d); 7.35 (5H,m); 7.60 (1H,d); 7.80 (1H,dd).

(v) 2-[N-(cyclopropyl)methyl-N-methylsulphamoyl]-pyrid-6-one.

$^1$H NMR ($CDCl_3$): 0.20 (2H,m); 0.55 (2H,m); 0.95 (1H,m); 2.95 (3H,s); 3.05 (2H,d); 6.81 (1H,d); 7.00 (1H,d); 7.60 (1H,t).

EXAMPLE 36

2-[N,N-dipropylsulphamoyl]-6-(methanesulphonyloxy)pyridine (Compound No. 36).

$^1$H NMR ($CDCl_3$): 0.90 (6H,t); 1.60 (4H,m); 3.25 (4H,t); 3.55 (3H,s); 7.25 (1H,d); 7.95 (1H,d); 8.05 (1H,t).

(iii) 2-[N,N-dipropylsulphamoyl]-6-fluoropyridine.

$^1$H NMR ($CDCl_3$): 0.90 (6H,t); 1.6 (4H,m); 3.25 (4H,t) 7.15 (1H,dd); 7.85 (1H,dd); 8.05 (1H,dd).

(iv) 2-[N,N-dipropylsulphamoyl]-6-(benzyloxy)pyridine.

$^1$H NMR ($CDCl_3$): 0.85 (6H,t); 1.55 (4H,m); 3.15 (4H,t); 5.40 (2H,s); 6.95 (1H,d); 7.30 (5H,m); 7.55 (1H,d); 7.75 (1H,t).

(v) 2-[N,N-dipropylsulphamoyl]pyrid-6-one.

$^1$H NMR ($CDCl_3$): 0.90 (6H,t); 1.60 (4H,m); 3.20 (4H,t); 6.82 (1H,d); 7.00 (1H,d); 7.60 (1H,dd).

EXAMPLE 37

2-[N,N-diethylsulphamoyll]-6-methanesulphonyloxy)-pyridine (Compound No. 37).

$^1$H NMR ($CDCl_3$): 1.2 (6H,t); 3.4 (4H,q); 3.55 (3H,s); 7.25 (1H,d); 7.9 (1H,d); 8.05 (1H,t).

(v) 2-[N,N-diethylsulphamoyl]pyrid-6-one.

$^1$H NMR ($CDCl_3$): 1.15 (6H,t); 3.35 (4H,q); 6.84 (1H,d); 7.04 (1H,d); 7.6 (1H,dd).

EXAMPLE 38

2-[N-methyl-N-propylsulphamoyl]-6-(methanesulphonyloxy)pyridine (Compound No. 38).

$^1$H NMR ($CDCl_3$): 0.95 (3H,t); 1.60 (2H,m); 2.95 (3H,s); 3.18 (2H,t); 3.55 (3H,s); 7.28 (1H,d); 7.90 (1H,d); 8.06 (1H,t).

(iii) 2-[N-methyl-N-propylsulphamoyl]-6-fluoropyridine.

$^1$H NMR ($CDCl_3$): 0.95 (3H,t); 1.60 (2H,m); 2.95 (3H,s); 3.25 (2H,t); 7.18 (1H,dd); 7.85 (1H,dd); 8.08 (1H,dd).

(iv) 2-[N-methyl-N-propylsulphamoyl]-6-benzyloxypyridine.

$^1$H NMR ($CDCl_3$): 0.90 (3H,t); 1.55 (2H,m); 2.85 (3H,s); 3.10 (2H,t); 5.40 (2H,s); 6.98 (1H,d); 7.35 (5H,m); 7.55 (1H,d); 7.75 (1H,t).

(v) 2-[N-methyl-N-propylsulphamoyl]pyrid-6-one.

$^1$H NMR ($CDCl_3$): 0.95 (3H,t); 1.60 (2H,m); 2.85 (3H,s); 3.16 (2H,t); 6.88 (1H,d); 7.00 (1H,d); 7.60 (1H,dd).

EXAMPLE 39

2-[N,N-dimethylsulphamoyl]-6-(methansulphonyloxy)-pyridine (Compound No. 39).

$^1$H NMR ($CDCl_3$): 2.92 (6H,s); 3.55 (3H,s); 7.27 (1H,d); 7.90 (1H,d); 8.06 (1H,t).

(v) 2-[N,N-dimethylsulphamoyl]pyrid-6-one.

This compound was prepared by bis-methylation of 2-sulphamoylpyrid-6-one using dimethylsulphate under standard conditions.

$^1$H NMR ($CDCl_3$): 2.88 (6H,s); 6.90 (1H,d); 7.03 (1H,d 7.65 (1H,dd).

EXAMPLE 40

2-[N-(2-methylpropyl)sulphamoyl]-6-(methanesulphonyloxy)pyridine (Compound No 40).

$^1$H NMR ($CDCl_3$): 0.95 (6H,d); 1.75 (1H,m); 2.92 (2H,t); 3.50 (3H,s); 4.70 (1H,bt); 7.30 (1H,d); 7.95 (1H,d); 8.05 (1H,t).

(iii) 2-[N-(2-methylpropyl)sulphamoyl]-6-fluoropyridine.

$^1$H NMR ($CDCl_3$): 0.95 (6H,d); 1.80 (1H,m); 2.90 (2H,d); 7.15 (1H,dd); 7.90 (1H,dd); 8.05 (1H,dd).

(iv) 2-[N-(2-methylpropyl)sulphamoyl]-6-benzyloxypyridine.

$^1$H NMR ($CDCl_3$): 0.85 (6H,d); 1.65 (1H,m); 2.70 (2H,t); 4.80 (1H,bt); 5.40 (2H,s); 6.98 (1H,d); 7.35 (5H,m); 7.55 (1H,d); 7.75 (1H,t).

(v) 2-[N-(2-methylpropyl)sulphamoyl]pyrid-6-one.

$^1$H NMR ($CDCl_3$): 0.95 (6H,d); 1.80 (1H,m); 2.80 (2H,t); 6.2 (1H,bt); 6.80 (1H,d); 7.08 (1H,d); 7.65 (1H,t).

EXAMPLE 41

2-[N-ethyl-N-methylsulphamoyl]-6-(methanesulphonyloxy)pyridine (Compound No. 41).

$^1$H NMR ($CDCl_3$): 1.16 (3H,t); 2.95 (3H,s); 3.30 (2H,q); 3.55 (3H,s); 7.25 (1H,d); 7.90 (1H,d); 8.05 (1H,t).

(iii) 2-[N-ethyl-N-methylsulphamoyl]-6-fluoropyridine.

$^1$H NMR ($CDCl_3$): 1.16 (3H,t); 2.95 (3H,s); 3.38 (2H,q); 7.18 (1H,dd); 7.85 (1H,dd); 8.05 (1H,dd).

(iv) 2-[N-ethyl-N-methylsulphamoyl]-6-(benzyloxy)-pyridine.

$^1$H NMR ($CDCl_3$): 1.15 (3H,t), 2.88 (3H,s); 3.35 (2H,q); 5.40 (2H,s); 6.98 (1H,d); 7.40 (5H,m); 7.55 (1H,d); 7.75 (1H,dd).

(v) 2-[N-ethyl-N-methylsulphamoyl]pyrid-6-one.

$^1$H NMR ($CDCl_3$): 1.19 (3H,t); 2.90 (3H,s); 3.28 (2H,q); 6.82 (1H,d); 7.02 (1H,d); 7.60 (1H,dd).

EXAMPLE 42

2-[N-(3,3,3,2,2-pentafluoropropyl)sulphamoyl]-6-(methanesulphonyloxy)pyridine (Compound No. 42).

$^1$H NMR ($CDCl_3$): 3.50 (3H,s); 3.92 (2H,bt); 5.20 (1H,bs); 7.31 (1H,d); 7.95 (1H,d); 8.09 (1H,t).

(iii) 2[N-(3,3,3,2,2-pentafluoropropyl)sulphamoyl]-6-fluoropyridine.

$^1$H NMR ($CDCl_3$): 3.90 (2H,dt); 5.30 (1H,bt); 7.20 (1H,dd); 7.90 (1H,dd); 8.06 (1H,dd).

(iv) 2-[N-(3,3,3,2,2-pentafluoropropyl)sulphamoyl]-6(benzyloxy)pyridine.

$^1$H NMR ($CDCl_3$): 3.55 (2H,dt); 5.15 (1H,bt); 5.40 (2H,s); 7.04 (1H,d); 7.35 (5H,m); 7.55 (1H,d); 7.78 (1H,t).

(v) 2-[N-(3,3,3,2,2-pentafluoropropyl)sulphamoyl]-pyrid-6-one.

$^1H$ NMR (DMSO): 3.90 (2H,bt); 6.82 (1H,d); 7.30 (1H,d) 7.82 (1H,t).

EXAMPLE 43

2-[N-(3-chloroprop-1-yl)-N-methylsulphamoyl]-6-(methanesulphonyloxy)pyridine (Compound No. 43).

$^1H$ NMR ($CDCl_3$): 2.05 (2H,m); 2.95 (3H,s); 3.40 (2H,t); 3.55 (3H,s); 3.62 (2H,t); 7.28 (1H,d); 7.90 (1H,d); 8.05 (1H,t).

(iii) 2-N-[N-(3-chloroprop-1-yl)-N-methylsulphamoyl]-6-fluoropyridine (A).

Compound (A) was prepared by N-methylation of 2-[N-(3-chloroprop-1-yl)sulphamoyl]-6-fluoropyridine (B) using standard conditions.

(A) $^1H$ NMR ($CDCl_3$): 2.08 (2H,m); 2.98 (3H,s); 3.45 (2H,t); 3.64 (2H,t); 7.18 (1H,dd); 7.88 (1H,dd); 8.05 (1H,dd).

(B) $^1H$ NMR ($CDCl_3$): 2.03 (2H,m); 3.30 (2H,m); 3.62 (2H,t); 5.20 (1H,bs); 7.18 (1H,dd); 7.90 (1H,dd); 8.05 (1H,dd).

(iv) 2-[N-(3-chloroprop-1-yl)n-methylsulphamoyl]-6-(benzyloxy)pyridine.

$^1H$ NMR ($CDCl_3$): 2.08 (2H,m); 3.02 (3H,s); 3.38 (2H,t); 3.65 (2H,t); 5.50 (2H,s); 7.08 (1H,d); 7.40 (5H,m); 7.60 (1H,d) 7.85 (1H,t).

(v) 2-[N-(3-chloroprop-1-yl)-N-methylsulphamoyl]-pyrid-6-one.

$^1H$ NMR ($CDCl_3$): 2.05 (2H,m); 2.90 (3H,s); 3.35 (2H,t); 3.60 (2H,t); 6.89 (1H,d); 7.15 (1H,d); 7.68 (1H,t).

EXAMPLE 44

2-[N-(1,1,1-trifluoroprop-2-yl)sulphamoyl]-6-(methanesulphonyloxy)pyridine (Compound No 44).

$^1H$ NMR ($CDCl_3$): 1.30 (3H,d); 3.57 (3H,s); 4.00 (1H,m); 7.30 (1H,d); 7.95 (1H,d); 8.08 (1H,t); 8.60 (1H,bs).

(v) 2-[N-(1,1,1-trifluoroprop-2-yl)sulphamoyl]pyrid-6-one.

$^1H$ NMR ($CDCl_3$): 1.38 (3H,d); 4.00 (1H,m); 6.85 (2H,m); 7.09 (1H,d); 7.68 (1H,dd).

EXAMPLE 45

2-[N-(3,3,3-trifluoropropyl)sulphamoyl]-6-(methanesulphonyloxy)pyridine (Compound No. 45).

$^1H$ NMR ($CDCl_3$): 2.45 (2H,m); 3.45 (2H,q); 3.54 (3H,s); 5.10 (1H,bt); 7.32 (1H,d); 7.95 (1H,d); 8.09 (1H,t).

(iii) 2-[N-(3,3,3-trifluoropropyl)sulphamoyl]-6-fluoropyridine.

$^1H$ NMR ($CDCl_3$): 2.48 (2H,m); 3.45 (2H,q); 5.19 (1H,bt); 7.20 (1H,dd); 7.90 (1H,dd); 8.05 (1H,dd).

(v) 2-[N-(3,3,3-trifluoropropyl)sulphamoyl]pyrid-6-one.

A solution of 2-[N-(3,3,3-trifluoropropyl)sulphamoyl-6-(benzyloxy)pyridine (1.9 g) and trifluoroacetic acid (5 $cm^3$) in dichloromethane (5 $cm^3$) was stirred at the ambient temperature for 7 hours. The reaction mixture was partially evaporated under reduced pressure. Toluene (5 $cm^3$) was added and the reaction mixture evaporated to dryness. The crude product was purified using silica chromatography eluting with ethyl acetate containing 50% by volume hexane.

$^1H$ NMR ($CDCl_3$): 2.40 (2H,m); 3.28 (2H,q); 6.80 (1H,d); 7.20 (1H,bt); 7.28 (1H,d); 7.66 (1H,dd).

EXAMPLE 46

2-[N-methylsulphamoyl]-6-(methanesulphonyloxy)-pyridine (Compound No. 46).

$^1H$ NMR ($CDCl_3$): 2.82 (3H,d); 3.54 (3H,s); 4.75 (1H,m); 4.85 (1H,m); 7.30 (1H,d); 7.98 (1H,d); 8.06 (1H,t).

(iii) 2-[N-methylsulphamoyl]-6-fluoropyridine.

$^1H$ NMR ($CDCl_3$): 2.80 (3H,bs); 4.82 (1H,bs); 7.18 (1H,dd); 7.92 (1H,dd); 8.05 (1H,dd).

(v) 2-[N-methylsulphamoyl]pyrid-6-one.

$^1H$ NMR ($CDCl_3$): 2.75 (3H,bs); 6.12 (1H,m); 6.85 (1H,d); 7.12 (1H,d); 7.67 (1H,dd).

EXAMPLE 47

2-[N-methyl-N-(prop-2-yn-1-yl)sulphamoyl]-6-(methanesulphonyloxy)pyridine (Compound No. 47).

$^1H$ NMR ($CDCl_3$): 2.09 (1H,t); 3.09 (3H,s); 3.55 (3H,s); 4.12 (2H,d); 7.30 (1H,d); 7.93 (1H,d); 8.05 (1H,t).

(v) 2-[N-methyl-N-(prop-2-yn-1-yl)sulphamoyl]pyrid-6-one

This compound was prepared by the following sequence of reactions:

Stage 1: 2-(N-methylsulphamoyl)pyrid-6-one was silylated with dimethyl-(1,1-dimethylethyl)chlorosilane in the presence of imadazole under standard conditions to give 2-[N-methylsulphamoyl]-6-[dimethyl-(1,1-dimethylethyl)silyloxy]pyridine $^1H$ NMR ($CDCl_3$): 0.37 (6H,s); 1.05 (9H,s); 2.76 (3H,d); 4.56 (1H,m); 6.89 (1H,d); 7.59 (1H,d); 7.78 (1H,t).

Stage 2:

To a solution of 2-[N-methylsulphamoyl]-6-[dimethyl(1,1-dimethyl)silyloxy]pyridine (0.4 g) in tetrahydrofuran (15 $cm^3$) at −78° C. under an atmosphere of nitrogen was added a 2.5M solution of butyl lithium in hexane (0.56 $cm^3$) with stirring. A solution of prop-2-yn-1-yl bromide (0.2 g of an 80% solution in toluene) in tetrahydrofuran (5 $cm^3$) was added dropwise. The reaction mixture was allowed to warm to the ambient temperature and was then stirred for 17 hours. The reaction mixture was poured onto dilute aqueous hydrochloric acid and mixed by shaking. The product was then extracted into ethyl acetate. The combined organic layers were washed with brine, dried over anhydrous magnesium sulphate and the solvent evaporated under reduced pressure to produce a crude product. The product was purified by silica chromatography eluting with hexane containing ethyl acetate at a concentration gradually increased from 20–50% by volume to give 2-[N-methyl-N-(prop-2-yn-1-yl)sulphamoyl]pyrid-6-one.

$^1H$ NMR ($CDCl_3$): 2.20 (1H,t); 2.96 (3H,s); 4.15 (2H,d); 6.88 (1H,d); 7.12 (1H,d); 7.66 (1H,dd).

EXAMPLE 48

2-[N-(1,1-dimethylethyl)sulphamoyl]-6-(methanesulphamoyloxy)pyridine (Compound No 48).

$^1H$ NMR ($CDCl_3$): 1.24 (9H,s); 3.55 (3H,s); 4.90 (1H,bs); 7.28 (1H,d); 8.00 (2H,m).

EXAMPLE 49

4-[N-(prop-2-yl)sulphamoyl]-2-(methanesulphonyloxy)-pyridine (Compound No. 49).

$^1H$ NMR ($CDCl_3$) 1.15 (6H,d); 3.54 (3H,s); 3.60 (1H,m); 4.60 (1H,bd); 7.50 (1H,s); 7.70 (1H,d); 8.55 (1H,d).

(i) 4-[benzythio]-2-chloropyridine.

$^1H$ NMR ($CDCl_3$): 4.23 (2H,s); 7.10(1H,d); 7.20 (1H,bs); 7.44 (5H,m); 8.20 (1H,d).

(ii) 4-[N-(prop-2-yl)sulphamoyl]pyridine-2-sulphonyl chloride.

(iii) 4-[N-(prop-2-yl)sulphamoyl]-2-chloropyridine.

$^1H$ NMR ($CDCl_3$): 1.28 (6H,d); 3.58 (1H,m); 5.58 (1H,d); 7.70 (1H,d); 7.80 (1H,bs); 8.65 (1H,d).

(iv) 4-[N-(prop-2-yl)sulphamoyl]-2-(benzyloxy)pyridine.

$^1H$ NMR ($CDCl_3$): 1.25 (6H,d); 3.65 (1H,m); 5.58 (2H,s); 7.35–7.65 (7H,m); 8.45 (1H,d).

(v) 4-[N-(prop-2-yl)sulphamoyl]pyrid-2-one $^1H$ NMR ($CDCl_3$): 1.25 (6H,d); 3.60 (1H,m); 6.58 (1H,bd); 6.99 (1H,bd); 7.75 (1H,d).

EXAMPLE 50

This example illustrates the stages in the preparation of 1-[N-(prop-2-yl)sulphamoyl]-3-(methanesulphonyloxy)benzene (Compound No. 50).

$^1H$ NMR ($CDCl_3$) 1.1 (6H,d); 3.25 (3H,s); 3.50 (1H,m); 4.80 (1H,bd); 7.55 (2H,m); 7.85 (2H,m).

Stage 1: 3-[benzoyloxy]benzenesulphonyl chloride was prepared according to the method described by Kato et al, J. Pesticide Science, 13, 107–115 (1988).

Stage 2: 1-[N-(Prop-2-yl)sulphamoyl]-3-(benzoyloxy)benzene.

This compound was prepared from the product of stage 1 by a process similar to that described in stage (iii) of Example 1.

$^1H$ NMR ($CDCl_3$): 1.15 (6H,d); 3.55 (1H,m); 4.34 (1H,m); 7.45 (1H,m); 7.5–7,7 (4H,m); 7.80 (2H,m); 8.20 (2H,m).

Stage 3: 1-[N-(prop-2-yl)sulphamoyl]-3-hydroxybenzene.

A mixture of the product of stage 2 (0.18 g), 2M aqueous sodium hydroxide solution (15 $cm^3$) and tetrahydrofuran (15 $cm^3$) was stirred for 2 hours at the ambient temperature.

The reaction mixture was poured onto water and the organic layer was separated. The aqueous layer was acidified and extracted with ethyl acetate and the organic layers combined and washed with a basic aqueous wash to remove benzoic acid. The organic layers were then dried over anhydrous magnesium sulphate and the solvents evaporated under reduced pressure.

$^1H$ NMR ($CDCl_3$): 1.08 (6H,d); 3.45 (1H,m); 5.1 (1H,d); 7.08 (1H,m); 7.3–7.5 (3H,m).

EXAMPLE 51

This Example illustrates the stages in the preparation of 2-[N-(prop-2-yl)sulphenyl]-6-(methanesulphonyloxy)pyridine (Compound No. 51)

Stage 1: 2,6-bis-(methanesulphonyloxy)pyridine. 2,6-dihydroxypyridine hydrochloride (3 g) was suspended in dichloromethane (250 $cm^3$) under an atmosphere of nitrogen at 0° C. The mixture was treated with methanesulphonyl chloride (3.5 $cm^3$). The suspension was stirred and triethylamine (9.4 $cm^3$) was added in aliquots over 15 minutes. The resulting mixture was stirred for 17 hours and poured onto brine. The organic layer was separated, washed twice with brine, dried over anhydrous magnesium sulphate, and the solvent evaporated under reduced pressure.

$^1H$ NMR ($CDCl_3$): 3.5 (6H,s); 7.03 (2H,d); 7.95 (1H,dd).

Stage 2: 2-(benzylthio)-6-(methanesulphonyloxy)-pyridine.

A solution of sodium benzylthiolate (0.002 moles, 0.292 g) in dimethylformamide (7.5 $cm^3$) was added dropwise to a solution of the product of stage 1 in dimethylformamide (5 $cm^3$) under an atmosphere of nitrogen at 0° C. The resulting solution was stirred at the ambient temperature for 15 minutes. The reaction mixture was poured onto brine, and the product extracted into diethyl ether. The combined organic layers were washed with brine, dried over anhydrous magnesium sulphate, filtered and the solvent evaporated under reduced pressure to leave the crude product.

The product was purified by silica chromatography eluting with hexane containing 33% by volume diethyl ether.

$^1H$ NMR ($CDCl_3$): 3.30 (3H,s); 4.39 (2H,s); 6.80 (1H,d); 7.17 (1H,d); 7.30 (5H,m); 7.60 (1H,dd).

Stage 3: 2-[N-(prop-2-yl)sulphenyl]-6-(methanesulphonyloxy)pyridine (Compound No. 51).

The product of stage 2 (0.07 g) was dissolved in dichloromethane (1 $cm^3$) at room temperature under an atmosphere of nitrogen and a solution of sulphuryl chloride in dichloromethane (1 $cm^3$) added in portions. After 30 minutes the reaction mixture was added to a solution of 2-aminopropane (0.4 $cm^3$) in dichloromethane (10 $cm^3$) with stirring. The mixture was allowed to stand for 17 hours, and was then washed with brine and dried over anhydrous magnesium sulphate. The solvent was evaporated under reduced pressure and the crude product purified by silica chromatography, eluting with hexane containing 33% by volume diethyl ether, to give the title product.

$^1H$ NMR ($CDCl_3$): 1.20 (6H,d); 3.00 (1H,m); 3.18 (1H,m); 3.48 (3H,s); 6.78 (1H,d); 7.40 (1H,d); 7.69 (1H,dd).

EXAMPLE 52

This Example illustrates the preparation of 2-[N-(prop-2-yl)sulphinyl]-6(methanesulphonyloxy)pyridine (Compound No. 52).

A solution of 2-[N-(prop-2-yl)sulphenyl]-6-(methanesulphonyloxy)pyridine (0.055 g) in dichloromethane (2 $cm^3$) was cooled to −78° C. and a solution of m-chloroperbenzoic acid (0.04 g) in dichloromethane (2 $cm^3$) was added. After 1 hour, the reaction mixture was poured into an aqueous solution of sodium bicarbonate. The organic layer was separated, washed with aqueous sodium bicarbonate solution and brine and then dried over anhydrous magnesium sulphate. Evaporation of the solvent under reduced pressure gave a crude product which was purified by silica chromatography, eluting with hexane containing 50% by volume ethyl acetate.

$^1H$ NMR ($CDCl_3$): 1.12 (3H,d); 1.30 (3H,d); 3.55 (3H,s); 3.58 (1H,m); 4.18 (1H,bd); 7.24 (1H,m); 8.02 (2H,m).

EXAMPLE 53

This Example illustrates an emulsifiable concentrate composition which is readily convertible by dilution with water into a liquid preparation suitable for spraying purposes. The concentrate has the following composition:

| | % Weight |
|---|---|
| Compound No 1 | 25.0 |
| SYNPERONIC NP13 (nonylphenol-ethyleneoxide condensate; Synperonic is a registered trade mark) | 2.5 |
| Calcium dodecylbenzenesulphonate | 2.5 |
| AROMASOL H (alkylbenzene solvent; Aromasol is a registered trade mark) | 70 |

EXAMPLE 54

This Example illustrates an emulsifiable concentrate composition which is readily convertible by dilution with water into a liquid preparation suitable for spraying purposes. The concentrate has the following composition:

| | % Weight |
|---|---|
| Compound No 3 | 50.0 |
| SYNPERONIC NP13 (nonylphenol-ethyleneoxide condensate; Synperonic is a registered trade mark) | 6.0 |
| Calcium dodecylbenzenesulphonate | 4.0 |
| AROMASOL H (alkylbenzene solvent; Aromasol is a registered trade mark) | 40.0 |

EXAMPLE 55

This Example illustrates an emulsifiable concentrate composition which is readily convertible by dilution with water into a liquid preparation suitable for spraying purposes. The concentrate has the following composition:

| | % Weight |
|---|---|
| Compound No 5 | 1.0 |
| SYNPERONIC OP10 (octylphenol-ethyleneoxide condensate; Synperonic is a registered trade mark) | 3.0 |
| Calcium dodecylbenzenesulphonate | 2.0 |
| AROMASOL H (alkylbenzene solvent; Aromasol is a registered trade mark) | 94.0 |

EXAMPLE 56

This Example illustrates a wettable powder composition which is readily convertible by dilution with water into a liquid preparation suitable for spraying purposes. The wettable powder has the following composition:

| | % Weight |
|---|---|
| Compound No 46 | 25.0 |
| Silica | 25.0 |
| Sodium lignosulphonate | 5.0 |
| Sodium lauryl sulphate | 2.0 |
| Kaolinite | 43.0 |

EXAMPLE 57

This Example illustrates a wettable powder composition which is readily convertible by dilution with water into a liquid preparation suitable for spraying purposes. The wettable powder has the following composition:

| | % Weight |
|---|---|
| Compound No. 11 | 1.0 |
| Sodium lignosulphonate | 5.0 |
| Sodium lauryl sulphate | 2.0 |
| Kaolinite | 92.0 |

EXAMPLE 58

This Example illustrates a wettable powder composition which is readily convertible by dilution with water into a liquid preparation suitable for spraying purposes. The wettable powder has the following composition:

| | % Weight |
|---|---|
| Compound No 42 | 40.0 |
| Silica | 40.0 |
| Calcium lignosulphonate | 5.0 |
| Sodium lauryl sulphate | 2.0 |
| Kaolinite | 13.0 |

EXAMPLE 59

This Example illustrates a dusting powder which may be applied directly to plants or other surfaces and comprises 1% by weight of Compound 48 and 99% by weight of talc.

EXAMPLE 60

This Example illustrates a concentrated liquid formulation suitable for application by ultra low volume techniques after mixing with paraffinic diluents.

| | % Weight |
|---|---|
| Compound No 45 | 90.0 |
| SOLVESSO 200 (inert diluent; Solvesso is a registered trade mark) | 10.0 |

EXAMPLE 61

This Example illustrates a concentrated liquid formulation suitable for application by ultra low volume techniques after mixing with paraffinic diluents.

| | % Weight |
|---|---|
| Compound No 44 | 25.0 |
| SOLVESSO 200 (inert diluent; Solvesso is a registered trade mark) | 75.0 |

EXAMPLE 62

This Example illustrates a concentrated liquid formulation suitable for application by ultra low volume techniques after mixing with paraffinic diluents.

| | % Weight |
|---|---|
| Compound No 40 | 10.0 |
| SOLVESSO 200 (inert diluent; Solvesso is a registered trade mark) | 90.0 |

EXAMPLE 63

This Example illustrates a capsule suspension concentrate which is readily convertible by dilution with water to form a preparation suitable for application as an aqueous spray.

| | % Weight |
|---|---|
| Compound No 1 | 10.0 |
| Alkylbenzene solvent (e.g. AROMASOL H) | 5.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL; Keltrol is a registered trade mark) | 0.1 |
| Water | 76.4 |

EXAMPLE 64

This Example illustrates a capsule suspension concentrate which is readily convertible by dilution with water to form a preparation suitable for application as an aqueous spray.

| | % Weight |
|---|---|
| Compound No 5 | 1.0 |
| Alkylbenzene solvent (e.g. AROMASOL H) | 10.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL; Keltrol is a registered trade mark) | 0.1 |
| Water | 80.4 |

EXAMPLE 65

A ready for use granular formulation:

| | % Weight |
|---|---|
| Compound No 1 | 0.5 |
| SOLVESSO 200 | 0.2 |
| nonylphenol ethoxylate (e.g. Synperonic NP8) | 0.1 |
| Calcium carbonate granules (0.3-0.7 mm) | 99.2 |

EXAMPLE 66

An aqueous suspension concentrate:

| | % Weight |
|---|---|
| Compound No 48 | 5.0 |
| Kaolinite | 15.0 |
| Sodium lignosulphonate | 3.0 |
| nonylphenol ethoxylate (e.g. Synperonic NP 8) | 1.5 |
| propylene glycol | 10.0 |
| Bentonite | 2.0 |
| Polysaccharide (e.g. Keltrol) | 0.1 |
| Bactericide (e.g. Proxel; Proxel is a registered Trade Mark) | |
| Water | 63.3 |

EXAMPLE 67

A ready for use dust (D.P.) made from a concentrate

| | % Weight |
|---|---|
| Concentrate: | |
| Compound No 2 | 10 |
| Silica | 20 |
| Magnesium Carbonate | 70 |
| Dust Example containing 1% active ingredient: | |
| Above concentrate | 10 |
| Talc | 90 |

EXAMPLE 68

This Example illustrates a liquid formulation suitable for direct application by ultra low volume techniques.

| | % weight |
|---|---|
| Compound No 41 | 15.0 |
| Cotton seed oil | 50.0 |
| SOLVESSO 200 (inert diluent; SOLVESSO is a registered trade mark) | 35.0 |

EXAMPLE 69

This Example illustrates a ready for use granule formulation.

| | % weight |
|---|---|
| Compound No 1 | 5.0 |
| SYNPERONIC NP8 (nonylphenol-ethyleneoxide condensate; SYNPERONIC is a registered trade mark) | 2.0 |
| Pumice granules (20/40 BS Mesh) | 93.0 |

EXAMPLE 70

This Example illustrates a water dispersible granule formulation

| | % Weight |
|---|---|
| Compound No 1 | 5.0 |
| Sodium lignosulphonate | 5.0 |
| Sodium dioctylsulphosuccinate | 5.0 |
| Sodium acetate | 10.0 |
| Montmorillonite powder | 65.0 |

EXAMPLE 71

This Example illustrates the insecticidal properties of the products of this invention.

The activity of the product was determined using a variety of insect pests. The product were used in the form of liquid preparations containing 500, 250 or 100 parts per million (ppm) by weight of the product. The preparations were made by dissolving the product in acetone and diluting the solutions to give the required concentration of product using as a diluent water containing 0.01% by weight of a nonylphenol ethoxylate wetting agent sold under the trade name SYNPERONIC NX (registered trade mark).

The test procedure adopted with regard to each pest was essentially the same and comprised supporting a number of the pests on a medium which was usually a host plant or a foodstuff on which the pests feed, and treating either or both of the pests and the medium with the preparations. The mortality of the insects was then assessed at periods varying from 1 to 6 days after the treatment.

The results of the tests are given in Table III for each of the products, at the rate of application indicated (in ppm) in the second column of the Table, as a grading of observed mortality designated as A, B or C, wherein A indicates 80-100% mortality, B indicates 50-79% mortality, and C indicates less than 50% mortality.

In Table III, the test type is designated by a letter code, and the species, support medium, type and duration of the test are given for each code in Table II.

TABLE II

| CODE LETTERS | TEST SPECIES | SUPPORT MEDIUM/ FOOD | TYPE OF TEST | DURATION (DAYS) |
|---|---|---|---|---|
| MP | *Myzus persicae* (aphids) | French bean leaf | Contact | 3 |
| NC (2DAT) | *Nephotettix cincticeps* (green leafhopper-nymphs) | Rice plant | Contact | 2 |
| (6DAT) | *Nephotettix cincticeps* (green leafhopper-nymphs) | " | " | 6 |
| HV (2DAT) | *Heliothis virescens* (tobacco budworm-larvae) | Cotton leaf | Residual | 2 |
| (6DAT) | *Heliothis virescens* (tobacco budworm-larvae) | " | " | 6 |
| SP (2DAT) | *Spodoptera exigua* (lesser army worm-larvae) | Cotton leaf | " | 2 |
| (6DAT) | *Spodoptera exigua* (lesser army worm-larvae) | " | " | 6 |
| DB | *Diabrotica balteata* (rootworm-larvae) | Filter paper/ maize seed | Residual | 2 |

"Contact" indicates a test in which both the medium and the pests were treated. "Residual" indicates a test in which the medium was treated prior to infestation with the pests.

TABLE III

| COMPOUND | RATE | | NC | | HV | | SP | | |
|---|---|---|---|---|---|---|---|---|---|
| No. | (ppm) | MP | 2DAT | 6DAT | 2DAT | 6DAT | 2DAT | 6DAT | DB |
| 1 | 500 | A | A | — | B | B | C | C | B |
| 2 | 500 | C | A | — | A | — | C | C | A |
| 3 | 500 | C | A | — | C | B | B | B | A |
| 4 | 500 | C | B | A | C | C | C | C | C |
| 5 | 500 | C | A | — | C | C | C | C | A |
| 6 | 500 | C | C | C | C | C | C | C | B |
| 7 | 500 | C | C | C | C | A | C | C | C |
| 8 | 500 | C | A | — | C | C | C | C | A |
| 9 | 500 | C | A | — | C | C | A | — | B |
| 10 | 500 | C | C | C | C | C | C | C | C |
| 11 | 100 | C | A | — | C | C | — | — | C |
| 12 | 100 | C | C | B | C | C | — | — | C |
| 13 | 100 | C | B | B | C | C | C | C | C |
| 14 | 500 | C | A | — | C | C | C | C | C |
| 15 | 500 | C | A | — | C | C | B | B | C |
| 16 | 500 | C | C | C | A | — | C | C | B |
| 17 | 500 | C | A | — | C | C | C | C | C |
| 18 | 500 | C | C | C | C | C | C | C | C |
| 19 | 500 | C | C | A | C | C | C | C | C |
| 20 | 500 | C | B | A | C | C | C | C | B |
| 21 | 500 | C | C | C | C | C | C | C | C |
| 22 | 100 | C | C | C | C | C | B | B | C |
| 23 | 100 | C | C | C | C | C | B | B | C |
| 24 | 500 | C | C | — | C | C | B | A | C |
| 25 | 100 | C | B | B | C | C | C | C | C |
| 26 | 500 | C | A | — | C | C | C | C | A |
| 27 | 500 | C | C | — | C | A | C | C | C |
| 28 | 100 | C | B | — | C | C | C | C | C |
| 29 | 500 | C | B | — | C | C | C | C | C |
| 30 | 500 | C | C | — | C | C | C | C | C |
| 31 | 500 | C | B | A | C | C | C | A | A |
| 32 | 500 | A | B | B | C | C | C | A | C |
| 33 | 500 | C | C | A | C | C | C | C | C |
| 34 | 500 | C | A | — | C | C | B | B | B |
| 35 | 500 | C | A | — | B | B | C | C | A |
| 36 | 500 | C | A | — | C | C | C | C | A |
| 37 | 500 | A | A | — | B | A | C | C | A |
| 38 | 500 | C | B | A | A | — | C | A | B |
| 39 | 500 | B | B | A | C | C | C | C | A |
| 40 | 500 | C | A | — | C | C | C | C | C |
| 41 | 500 | C | A | — | B | A | C | C | A |
| 42 | 500 | C | A | — | B | B | C | C | B |
| 43 | 100 | C | A | — | C | B | C | C | A |
| 44 | 500 | C | A | — | C | C | C | C | C |
| 45 | 500 | C | A | — | C | C | C | C | C |
| 46 | 100 | C | C | B | B | A | C | C | B |
| 47 | 500 | C | A | — | A | — | A | — | A |
| 48 | 500 | C | B | A | C | C | C | C | B |

TABLE III-continued

| COMPOUND No. | RATE (ppm) | MP | NC 2DAT | NC 6DAT | HV 2DAT | HV 6DAT | SP 2DAT | SP 6DAT | DB |
|---|---|---|---|---|---|---|---|---|---|
| 49 | 500 | C | A | — | C | C | C | C | C |
| 50 | 100 | C | B | B | C | C | A | — | C |
| 51 | 100 | C | C | C | C | C | B | B | C |
| 52 | 500 | C | A | — | C | B | C | C | A |

What is claimed is:

1. A compound of formula (I):

(I)

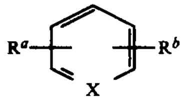

wherein X is nitrogen or carbon bearing a hydrogen atom; $R^a$ is a group of formula $(R^1)(R^2)NS(O)_n$— wherein $R^1$ and $R^2$ are independently selected from hydrogen, $C_{1-8}$ alkyl, $C_{1-6}$ haloalkyl, $C_{1-6}$ alkoxy, $C_{1-6}$ alkoxyalkyl, formyl, $C_{2-6}$ alkanoyl, $C_{2-8}$ alkenyl, $C_{2-8}$ alkynyl, $C_{3-6}$ cycloalkyl, $C_{3-6}$ cycloalkylmethyl, phenyl and benzyl, and n is 0, 1 or 2; $R^b$ is a group of formula $—OSO_2R^3$ wherein $R^3$ is selected from $C_{1-8}$ alkyl, $C_{1-4}$ alkyl substituted by a phenyl group, $C_{1-8}$ haloalkyl, $C_{2-6}$ alkenyl, $C_{2-4}$ alkenyl substituted by a phenyl group, phenyl optionally substituted by methyl, trifluoromethyl or methoxy, pyridyl optionally substituted by fluorine, thienyl, and a group of formula $—N(R^4)(R^5)$ wherein $R^4$ and $R^5$ are independently selected from hydrogen and $C_{1-4}$ alkyl; and wherein the groups $R^a$ and $R^b$ occupy either a 1,3 configuration relative to each other on the ring when X is carbon bearing a hydrogen, or a 2,4 or 2,6 configuration relative to the group X when X is nitrogen.

2. A compound as claimed in claim 1 wherein each of the groups $R^1$ and $R^2$ is independently selected from hydrogen, $C_{1-7}$ alkyl, $C_{1-4}$ haloalkyl, $C_{1-4}$ alkoxy, $C_{2-4}$ alkoxyalkyl, formyl, $C_{2-4}$ alkanoyl, $C_{2-4}$ alkenyl, $C_{2-4}$ alkynyl, $C_{3-6}$ cycloalkyl, $C_{3-6}$ cycloalkylmethyl, phenyl and benzyl.

3. A compound as claimed in claim 1 or claim 2 wherein the group $R^3$ is $C_{1-4}$ alkyl, $C_{1-2}$ alkyl substituted with a phenyl group, $C_{1-6}$ haloalkyl, $C_{2-4}$ alkenyl, ethenyl substituted with a phenyl group, phenyl optionally substituted by methyl, trifluoromethyl or methoxy, pyridyl optionally substituted by fluorine, 2-thienyl, 3-thienyl or a group of formula $—N(R^4)(R^5)$ wherein $R^4$ and $R^5$ are independently selected from hydrogen and $C_{1-4}$ alkyl.

4. A compound as claimed in claim 1 wherein the value of n is 2.

5. A compound as claimed in claim 1 wherein the group X is nitrogen.

6. A compound as claimed in claim 5 wherein the groups $R^a$ and $R^b$ occupy a 2,6 configuration relative to the group X.

7. A compound as claimed in claim 1 having the formula (IA):

(IA)

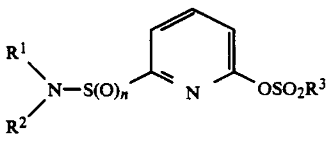

wherein $R^1$ and $R^2$ are independently selected from hydrogen, $C_{1-6}$ alkyl, $C_{1-6}$ haloalkyl, $C_{1-6}$ alkoxy, $C_{1-6}$ alkoxyalkyl, formyl, $C_{2-6}$ alkanoyl, $C_{3-6}$ cycloalkyl, phenyl and benzyl; $R^3$ is selected from $C_{1-6}$ alkyl, $C_{1-6}$ haloalkyl and a group of formula $—N(R^4)(R^5)$ where $R^4$ and $R^5$ are independently selected from hydrogen and $C_{1-6}$ alkyl; and n is selected from 0, 1 and 2.

8. An insecticidal composition comprising an insecticidally effective amount of a compound as claimed in claim 1 in association with an insecticidally inert diluent or carrier.

9. A method of controlling insect pests at a locus which comprises application to the locus of an insecticidally effective amount of a composition as claimed in claim 8.

* * * * *